(12) United States Patent
Bierman et al.

(10) Patent No.: US 8,657,791 B2
(45) Date of Patent: Feb. 25, 2014

(54) CATHETER SECUREMENT DEVICE

(75) Inventors: Steven F. Bierman, Del Mar, CA (US); Richard A. Pluth, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 220 days.

(21) Appl. No.: 12/063,224

(22) PCT Filed: Aug. 22, 2006

(86) PCT No.: PCT/US2006/032846
§ 371 (c)(1),
(2), (4) Date: Feb. 7, 2008

(87) PCT Pub. No.: WO2007/024900
PCT Pub. Date: Mar. 1, 2007

(65) Prior Publication Data
US 2009/0143740 A1    Jun. 4, 2009

Related U.S. Application Data

(60) Provisional application No. 60/710,322, filed on Aug. 22, 2005.

(51) Int. Cl.
*A61M 5/32* (2006.01)
(52) U.S. Cl.
USPC ........................................................ 604/174
(58) Field of Classification Search
USPC .................................. 604/174–180
See application file for complete search history.

(56) References Cited

U.S. PATENT DOCUMENTS

| 3,782,383 | A |   | 1/1974 | Thompson et al. |
| 3,900,026 | A | * | 8/1975 | Wagner .......................... 128/888 |
| 4,351,331 | A |   | 9/1982 | Gereg |
| 4,405,163 | A |   | 9/1983 | Voges et al. |

(Continued)

FOREIGN PATENT DOCUMENTS

| EP | 0343821 | 11/1989 |
| EP | 0432880 | 6/1991 |

(Continued)

OTHER PUBLICATIONS

International Search Report for International Application No. PCT/US06/32846, mailed Sep. 13, 2007, 2 pages.

(Continued)

*Primary Examiner* — Kami A Bosworth
(74) *Attorney, Agent, or Firm* — Knobbe Martens Olson & Bear LLP

(57) ABSTRACT

A catheter securement device (100) holds a medical article such as a catheter hub or a connector fitting in position upon the body of a patient and at least inhibits longitudinal movement of the medical article. The securement device (100) includes a retainer (120) and at least one anchor pad (110). The retainer (120) has one or more curved ribs (280) into which at least a portion of the medical article is inserted. The retainer (120) includes a spine (145) that extends in a proximal direction from the retainer (120). The spine (145) includes a clip (147) having an abutment surface that can abut against a contact point or surface on the medical article. The abutment, in conjunction with a second abutment and/or a tapering shape of the retainer (120), inhibits longitudinal movement of the medical article in both proximal and distal directions.

18 Claims, 25 Drawing Sheets

(56) References Cited

U.S. PATENT DOCUMENTS

| | | |
|---|---|---|
| 4,435,175 A | 3/1984 | Friden |
| 4,699,616 A | 10/1987 | Nowak et al. |
| 4,752,292 A * | 6/1988 | Lopez et al. ............ 604/244 |
| 4,792,163 A | 12/1988 | Kulle |
| 4,898,587 A | 2/1990 | Mera |
| 4,903,995 A | 2/1990 | Blenkush et al. |
| 4,932,943 A | 6/1990 | Nowak |
| 4,944,728 A | 7/1990 | Carrell et al. |
| 4,981,475 A | 1/1991 | Haindl |
| 5,024,665 A | 6/1991 | Kaufman |
| 5,053,015 A | 10/1991 | Gross |
| 5,073,170 A | 12/1991 | Schneider |
| 5,084,026 A | 1/1992 | Shapiro |
| 5,135,505 A | 8/1992 | Kaufman |
| 5,154,699 A | 10/1992 | Ryan |
| 5,192,273 A | 3/1993 | Bierman |
| 5,267,967 A | 12/1993 | Schneider |
| 5,290,248 A | 3/1994 | Bierman et al. |
| 5,314,411 A | 5/1994 | Bierman et al. |
| 5,346,479 A | 9/1994 | Schneider |
| 5,354,282 A | 10/1994 | Bierman |
| 5,468,228 A | 11/1995 | Gebert |
| 5,490,504 A | 2/1996 | Vrona et al. |
| 5,522,803 A | 6/1996 | Teissen-Simony |
| 5,755,225 A | 5/1998 | Hutson |
| 5,810,398 A | 9/1998 | Matkovich |
| 5,916,200 A | 6/1999 | Eppley et al. |
| 6,123,690 A | 9/2000 | Mejslov |
| 6,231,548 B1 | 5/2001 | Bassett |
| 6,290,676 B1 | 9/2001 | Bierman |
| 6,387,076 B1 | 5/2002 | Landuyt |
| 6,572,586 B1 | 6/2003 | Wojcik |
| 6,783,520 B1 | 8/2004 | Candray et al. |
| 6,949,084 B2 | 9/2005 | Marggi et al. |
| 6,976,980 B2 | 12/2005 | Brenner et al. |
| 7,014,627 B2 | 3/2006 | Bierman |
| 7,220,241 B2 | 5/2007 | Csincsura et al. |
| 7,303,544 B2 | 12/2007 | Bütikofer et al. |
| 7,377,472 B2 | 5/2008 | Brown et al. |
| 8,251,956 B2 | 8/2012 | Bierman et al. |
| 2001/0049490 A1 | 12/2001 | Slanda et al. |
| 2002/0161332 A1 | 10/2002 | Ramey |
| 2003/0212385 A1 | 11/2003 | Brenner et al. |
| 2004/0102736 A1 | 5/2004 | Bierman |
| 2004/0204685 A1 | 10/2004 | Wright et al. |
| 2005/0038453 A1 | 2/2005 | Raulerson |
| 2005/0120523 A1 | 6/2005 | Schweikert |
| 2006/0100604 A1 | 5/2006 | Brenner et al. |
| 2006/0247577 A1 | 11/2006 | Wright |
| 2007/0043326 A1 | 2/2007 | Navarro et al. |
| 2007/0142784 A1 | 6/2007 | Dikeman et al. |
| 2007/0240721 A1 | 10/2007 | Ho et al. |
| 2008/0082052 A1 | 4/2008 | Schnell et al. |
| 2008/0171993 A1 | 7/2008 | Beran |

FOREIGN PATENT DOCUMENTS

| | | |
|---|---|---|
| EP | 0527961 | 2/1993 |
| EP | 0574163 | 12/1993 |
| FR | 2 922 458 A1 | 4/2009 |
| WO | WO 88/04185 | 6/1988 |
| WO | WO91/16939 | 11/1991 |
| WO | WO92/19314 | 11/1992 |
| WO | WO 00/48658 | 8/2000 |
| WO | WO02/083206 | 10/2002 |
| WO | WO03/051447 | 6/2003 |
| WO | WO 2004/016309 | 2/2004 |
| WO | WO 2004/022140 | 3/2004 |
| WO | WO2005/016413 | 2/2005 |
| WO | WO2007/117655 | 10/2007 |
| WO | WO2008/054761 | 5/2008 |
| WO | WO2008/058286 | 5/2008 |
| WO | WO2008/090233 | 7/2008 |
| WO | WO 2011/133818 | 10/2011 |

OTHER PUBLICATIONS

Extended European Search Report dated Oct. 14, 2010 for European Patent Application No. 06802125.2.

* cited by examiner

US 8,657,791 B2

CATHETER SECUREMENT DEVICE

RELATED APPLICATIONS

This application claims the benefit of U.S. Provisional Application No. 60/710,322, filed Aug. 22, 2005, which is hereby incorporated by reference in its entirety.

BACKGROUND

1. Field of the Invention

This invention relates to a securement system used to attach a medical line to a patient.

2. Description of the Related Art

It is common in the treatment of patients to utilize catheters to introduce fluids and medications directly into the patient or to withdraw fluids from the patient. Often, it becomes desirable to maintain such catheterization over an extended period of time during the treatment of a patient. In order to keep the catheter or other medical line properly positioned for the duration of treatment, the catheter or medical line can be secured to the patient in a variety of ways. Most commonly, this involves taping the catheter or medical line to the patient.

Securing a catheter with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheter upon the patient.

Taped dressings also require periodic changes. The frequent, often daily, removal and reapplication of adhesive tape to the skin of the patient can excoriate the skin in the area around the dressing. Such repeated applications of tape over the catheter or medical line can additionally lead to the build up of adhesive residue on the outer surface of the catheter or medical line. This residue can result in contaminants adhering to the catheter itself, increasing the likelihood of infection of the insertion site. This residue can also make the catheter or medical line stickier and more difficult to handle for healthcare providers.

SUMMARY OF THE INVENTION

The systems and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of the Preferred Embodiments" one will understand how the features of this invention provide several advantages over traditional catheter securement systems.

One aspect of the present invention is a medical line securement system that comprises a medical article that has a distal facing contact surface and a proximal facing contact surface. The system further comprises two anchor pads, each including a lower adhesive surface for attaching to an epidermal layer of a patient and a retainer. The retainer comprises two supports attached to the two anchor pads and a curved rib connecting the two supports. The rib has a downward facing interior shaped to retain at least a portion of the medical article and inhibit at least downward transverse movement of the medical article when the medical article is secured within the retainer. The rib has a first abutment disposed on a proximal side of the rib and contacts the distal facing contact surface of the medical article so as to inhibit distal longitudinal movement of the medical article if the medical article is slid in a distal longitudinal direction through the interior of the rib. The retainer further comprises a longitudinal access opening disposed on an underside of the curved rib to allow at least ingress of the portion of the medical article between the two supports and into the rib interior and a spine extending in a proximal direction from the rib. The spine has a clip spaced a distance from the rib. The clip has a second abutment disposed on a distal side of the clip and contacts the proximal facing contact surface of the medical article so as to inhibit proximal movement of the medical article if the medical article is slid in a proximal longitudinal direction through the interior of the rib.

Another aspect of the present invention is a medical line securement system that comprises a medical article that has a spin nut and a retainer. The retainer comprises a body member that has a channel formed therethrough. The channel has an inner surface and a longitudinal access opening disposed on an underside of the body member to allow ingress of the portion of the medical article into the channel. The retainer further comprises a first abutment that extends generally normal to an axis of the channel at a proximal end of the body member and is configured to inhibit longitudinal movement of the medical article in at least one direction. The retainer further comprises a spine that extends in a proximal direction from the body member and has a clip near a distal end of the spine. The clip has a second abutment disposed so as to face the first abutment. The second abutment is spaced a distance from the first abutment so as to receive the spin nut therebetween. The first and second abutments inhibit movement of the medical article if the medical article is slid in either longitudinal direction through the body member. The retainer further comprises at least one support surface disposed on the underside of the retainer and to a side of the access opening.

Another aspect of the present invention is a medical line securement system that comprises a medical article and two anchor pads. Each anchor pad includes a lower adhesive surface configured to attach to an epidermal layer of a patient. The system further comprises a retainer that has a body member. The body member has a channel formed therethrough about a channel axis. The channel is configured to retain at least a portion of the medical article and has a longitudinal access opening disposed on an underside of the body member to allow at least ingress of the portion of the medical article into the channel. The retainer further comprises a spine extending parallel to the channel axis and having an abutment on a distal end of the spine, the abutment extending generally normal to the channel axis and configured to inhibit longitudinal movement of the medical article. The system further comprises two supports disposed on the underside of the retainer and to both sides of the access opening opposite the channel axis, each support being attached to one of the two anchor pads.

Another aspect of the present invention is a retainer for securing a medical article that has a spin nut to a patient. The retainer comprises two anchor pads, each including a lower adhesive surface for attaching to an epidermal layer of a patient and two supports attached to the two anchor pads. The retainer further comprises a curved rib connecting the two supports and having a downward facing interior. The interior has a truncated cross-sectional shape and is configured to receive at least a portion of the medical article in a snap fit manner so as to inhibit at least downward transverse movement of the medical article when the medical article is secured within the retainer. The rib has a first abutment disposed on a proximal side of the rib. The retainer further comprises a longitudinal access opening disposed on an underside of the curved rib to allow at least ingress of the portion of the medical article between the two supports and into the rib interior. The retainer further comprises a spine that extends in a proximal direction from the rib and has a clip end. The clip end has a second abutment spaced a distance from the first abutment, the distance between the first abutment and the second abutment generally corresponding to a width of the spin nut.

DETAILED DESCRIPTION OF THE PREFERRED EMBODIMENTS

The following description and the accompanying figures, which describe and show the preferred embodiments, are made to demonstrate several possible configurations that a securement system can take to include various aspects and features of the invention. The illustrated embodiment is shown in use with an illustrative example of a connector fitting with a spin nut for connection to a catheter hub. The illustration of the securement device in this context is not intended to limit the disclosed aspects and features of the invention to the specified embodiments or to usage only with the illustrated connector. Those of skill in the art will recognize that the disclosed aspects and features of the invention are not limited to any particular embodiment of a securement system, and securement systems, which include one or more of the inventive aspects and features herein described, can be designed for use with a variety of medical articles.

Figure 1:
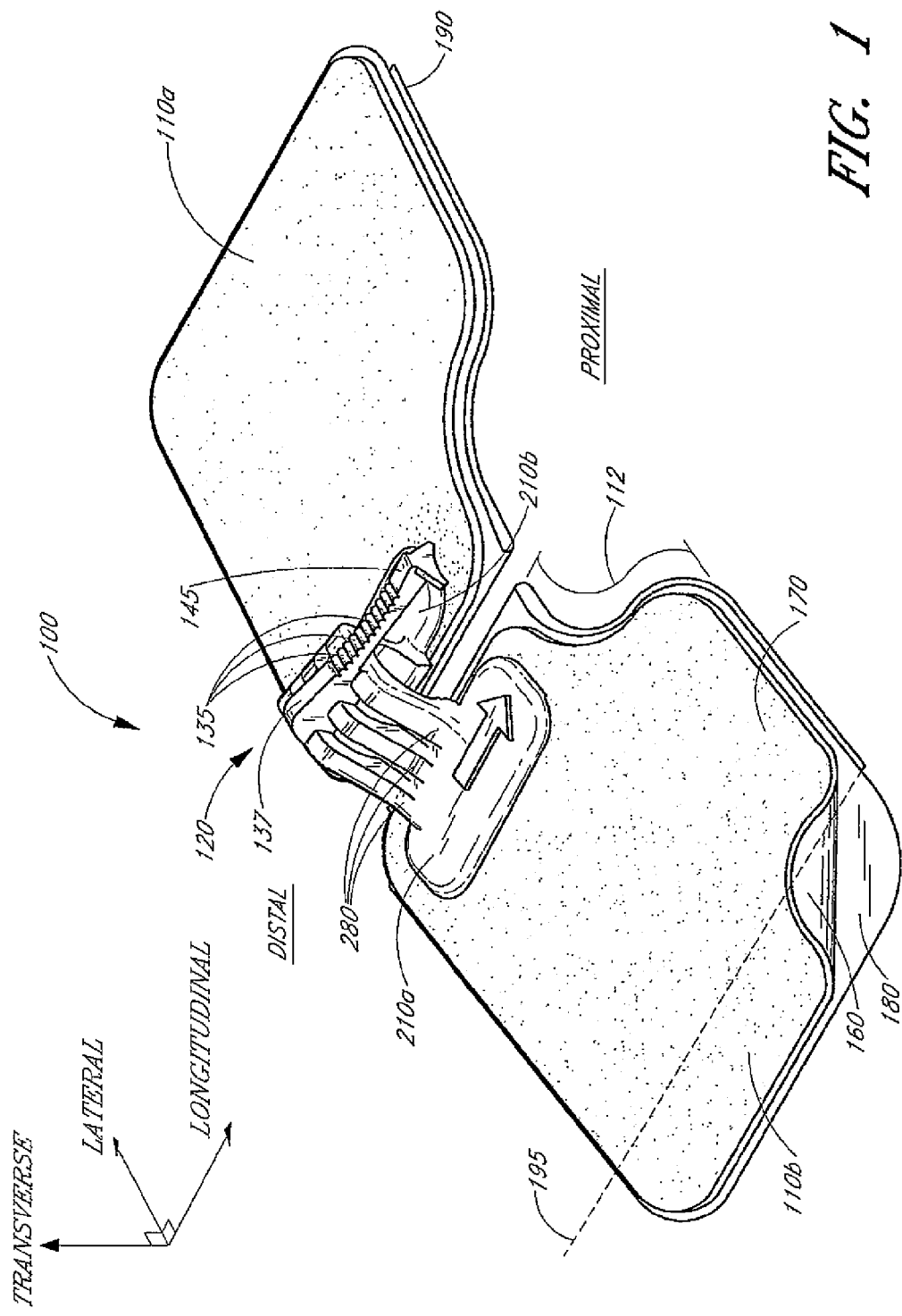
FIG. 1 is a perspective view of the securement device configured in accordance with a preferred embodiment of the present invention.

To assist in the description of these components of the securement system, the following coordinate terms are used (see FIG. 1). A "longitudinal axis" is generally parallel to a portion of the connector fitting or other medical article retained by the securement system, as well as parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel or connector fitting, and therefore is substantially synonymous with the term "longitudinal" as used herein. Also, the terms "proximal" and "distal", which are used to describe the present securement system, are used consistently with the description of the exemplary applications (i.e., the illustrative example of the use application). Thus, proximal and distal are used in reference to the center of the patient's body. The terms "upper," "lower," "top," "bottom," "underside," "upperside" and the like, which also are used to describe the present securement system; are used in reference to the illustrated orientation of the embodiment. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement systems, are now described. In the illustrated embodiment, the arrows on the securement device point in the direction toward the insertion site (i.e., in the proximal direction).

The preferred embodiments of the present invention advantageously provide a medical line securement system for securing a medical article to a patient. The medical article preferably has an elongated body. The elongated body cooperates with a retainer to arrest movement of the medical article in longitudinal, lateral, and transverse directions when placed within the retainer.

In each of the embodiments described below, the retainer has a body in the shape of one or more curved ribs. Each rib includes an interior for receiving a portion of the medical article. The rib interior has a longitudinal access opening located on an underside of the retainer. This access opening allows ingress or egress of the medical article. The medical article can be installed or removed from the underside of the retainer via this access opening. Such an arrangement allows the medical provider to align at least a portion of the medical article with the retainer prior to fixing the retainer to the patient's skin. In this way, the rib interior retains a portion of the medical article.

The retainer includes at least one abutment (preferably an abutment surface) that cooperates with at least one contact point or surface on the medical article. The one or more abutments of the retainer extend generally normal to the longitudinal axis and can be, for example, but without limitation a surface, a wall of a slot, a ridge, a protuberance, a lip of a clip, or like structures. The abutment cooperates wilt the one or more contact points or surfaces of the medical article to inhibit longitudinal movement of the medical article through the retainer.

At least one of the abutments is located at an end of a spine that extends from the body member in a proximal direction. The spine includes a clip having a ridge or lip which acts against at least a portion of a radially extending member or spin nut of the medical article. In this way, the medical article will be limited in its proximal movement (i.e., movement toward the patient) once the spin nut contacts or abuts against the clip of the retainer. The clip can have a unitary or non-unitary construction with the retainer body. The retainer may further include interengagement structure to couple the clip to the retainer body.

Ingress or egress of the medical article from the retainer may be facilitated by manipulation of the clip. For example, a healthcare provider can bend or flex the spine away from the medical article to ease ingress or egress of the medical article with the channel. For example, a medical article with a radially extending member in the form of a proximally located spin nut may be slid into or out of the rib interior along the longitudinal axis once the healthcare provider sufficiently bends the spine so that the clip does not interfere with the spin nut.

The retainer further inhibits distal movement of the retained medical article. A contact surface on the distal side of the spin nut can abut against an abutment surface in the form of a proximal end of the rib to inhibit distal movement (i.e., movement away from the patient). In certain embodiments, a step in the spin nut forms the contact surface. The step in the spin nut may be located between the distal and proximal ends of the spin nut. In certain embodiments, a step in the spin nut in combination with a contact surface on the distal side of the spin nut inhibits distal and proximal movement of the retained medical article.

The retainer of each embodiment described below further includes at least one support that is preferably disposed on the underside of the retainer at a position lower than the access opening. With this construction, the retainer holds the retained portion of medical article away from the patient's skin, when the retained portion is positioned within the rib interior, to avoid chaffing or excoriating the skin. The support in each of the illustrated embodiments includes left and right mounting wings that can be integral with the body member and are attached to left and right anchor pads. The lower surfaces of the left and right anchor pads attach to the patient's skin.

The retainer and anchor pad(s) also can have other constructions in order to inhibit contact between the skin and the retainer, as well as between the skin and the retained portion of the medical article. For example, the anchor pads can be thicker, in which case the mounting wings can be located higher on the retainer body.

To facilitate a complete understanding of the embodiment, the remainder of the detailed description describes the securement system with reference to the figures, wherein like elements among the embodiments are referenced with like numerals throughout the following description.

FIG. 1 is a perspective view of a securement device 100 configured in accordance with an embodiment of the present invention. As shown in FIG. 1, the illustrated securement device 100 comprises three main components: two anchor pads 110(a), 110(b) and a retainer 120. The illustrated retainer 120 includes a left footing/mounting wing 210(a) and right footing/mounting wing 210(b). Each mounting wing is disposed upon the respective one of the anchor pads 110(a), 110(b). The mounting wings 210(a), 210(b) extend in a lateral direction away from a center of the retainer 120.

As noted above, the securement device 100 can form a component of a catheterization or securement system that also includes one or more medical articles, such as connector fittings, catheters, hubs, catheter adaptors, fluid supply lines, or other articles suitable for securement via the anchor pads and retainer. An opening in the retainer 120 is aligned with the medical article. The medical article is inserted between the anchor pads 110(a), 110(b), through the opening, and into the retainer 120. The anchor pads 110(a), 110(b) are then secured to the skin of the patient, generally by an adhesive disposed upon the bottom surface of the pads. In this way, the retainer 120 secures the medical article to the patient. Thus, the retainer at least restricts, if not prevents, lateral and transverse movement of the retained section of the medical article. Additional features of the securement device 100 can restrict, if not prevent longitudinal movement of the retained section of the medical article. The embodiment illustrated is preferably for use with a connector fitting as described with reference to FIG. 5. The embodiments of the anchor pad and the retainer are described in more detail below.

Anchor Pad

FIG. 1 illustrates the anchor pads 110(b), 110(a) as part of the securement device 100. The general structure of each anchor pad 110(a), 110(b) comprises a generally rectangular shape with a scalloped region 112 located at a corner of each anchor pad. The scalloped configuration eases the process of aligning the securement device 100 with a catheter insertion site in the patient's skin. Although only a single shape of the anchor pad is illustrated in FIG. 1, those of skill in the art will recognize that a variety of shapes can be used.

Each anchor pad 110 desirably comprises a laminate structure with an upper plastic, paper or foam layer (e.g., closed-cell polyethylene foam) and a lower adhesive layer. The lower adhesive layer constitutes a lower surface 160 of the anchor pad. The lower surface 160 desirably is a medical-grade adhesive and can be either diaphoretic or nondiaphoretic, depending upon the particular application. Such foam with an adhesive layer is available commercially from Avery Dennison of Painsville, Ohio. While not illustrated, the anchor pads 110(*a*), 110(*b*) can include suture holes in addition to the adhesive layer to further secure the anchor pad to the patient's skin.

In other variations, a hydrocolloid adhesive or zinc oxide-based adhesive can advantageously be used upon the anchor pads 110(*a*), 110(*b*) for attaching the anchor pads to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, each anchor pad 110(*a*), 110(*b*) comprises a laminate structure with an upper woven layer and a lower adhesive layer. The upper layer can be polyester or other suitable polymer or textile materials. One particular suitable material is woven polyester available commercially under the name "Tricot" from Tyco. The lower adhesive layer constitutes the lower surface 160 of the anchor pad. The lower surface desirably is a medical-grade adhesive and can be either diaphoretic or nondiaphoretic, depending upon the particular application.

A surface of the upper foam layer constitutes an upper surface 170 of the anchor pads 110(*a*), 110(*b*). The upper surface 170 can be roughened by corona-treating the foam with a low electric charge. The roughened or porous upper surface can improve the quality of the adhesive joint (which is described below) between the mounting wings 210 and the anchor pads 110. In a further variation, the flexible anchor pad can comprise an upper paper or other woven or nonwoven cloth or plastic layer in lieu of a roughened upper foam surface.

As illustrated in FIG. 1, a removable paper or plastic release liner 180 desirably covers the adhesive lower surface 160 before use. The liner 180 preferably resists tearing and desirably is divided into a plurality of pieces to ease attachment of the pad to a patient's skin.

The liner 180 comprises a folded over portion to define a pull tab 190. The pull tab 190 can be utilized to remove the paper or plastic release liner 180 from their adhesive lower surface 160 before use. A healthcare provider uses the pull tab 190 by grasping and pulling on it so that the liner 180 is separated from the lower surface 160. The pull tab 190 overcomes any requirement that the healthcare provider pick at a corner edge or other segment of the liner in order to separate the liner from the adhesive layer.

The pull tab 190 of course can be designed in a variety of configurations. For example, the pull tab 190 can be located along a center line of the anchor pad 110; or alternatively, the pull tab can be located along any line of the anchor pad 110 in order to ease the application of the anchor pad onto the patient's skin at a specific site. For example, an area of a patient's skin with an abrupt bend, such as at a joint, can require that the pull tab 190 be aligned toward one of the lateral ends of the anchor pad 110 rather than along the center line. In the embodiment illustrated in FIG. 1, the pull tab 190 extends from a bottom surface of the anchor pads 110(*a*), 110(*b*) and along an outer line 195.

The fold that forms the pull tab 190 preferably occurs laterally beyond the inner (medial) edge on each anchor pad 110(*a*), 110(*b*), rather than at the inner edge of the anchor pad 110(*a*), 110(*b*). Thus, the spacing between the folds of the release liners 180 is less than the spacing between the inner edges of the anchor pads 110(*a*), 110(*b*). The projection of the release linear beyond the anchor pad inner edge provides an area onto which any adhesive, which is used to attach the retainer to the anchor pad, can run while lessening the occurrence of such adhesive contacting the fold. Cracks often occur at the fold and presence of adhesive in such cracks can create delimitation of the release liner and incomplete removal of the release linear when peeled away from the corresponding anchor pad 110(*a*), 110(*b*).

Additionally, the distal side of each release liner is cut to increase a "view window" through which a healthcare provider can see when aligning the retainer over the medical article (e.g., the catheter hub and/or the connector fitting). Preferably, the resulting relief originates from the inner edge of the release linear generally at a right angle thereto and then transitions into a shape that generally matches the shape of the adjacent region of corresponding anchor pad 110(*a*), 110(*b*). The initial right-angle cut of this relief reduces instances of the release linear ripping when properly pulled in the lateral direction away from the retainer 120.

Retainer

Figure 2:
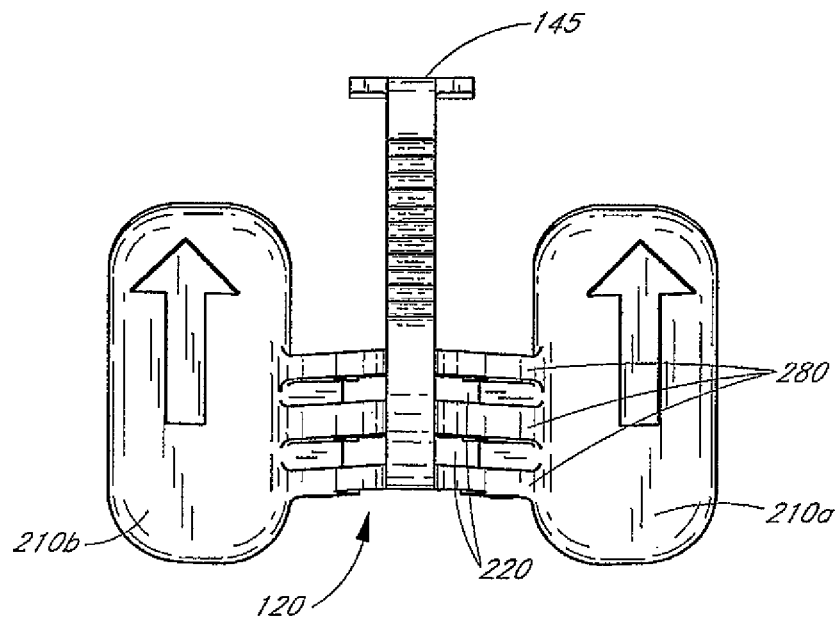
FIG. 2 is a top plan view of the retainer of FIG. 1.
Figure 3:
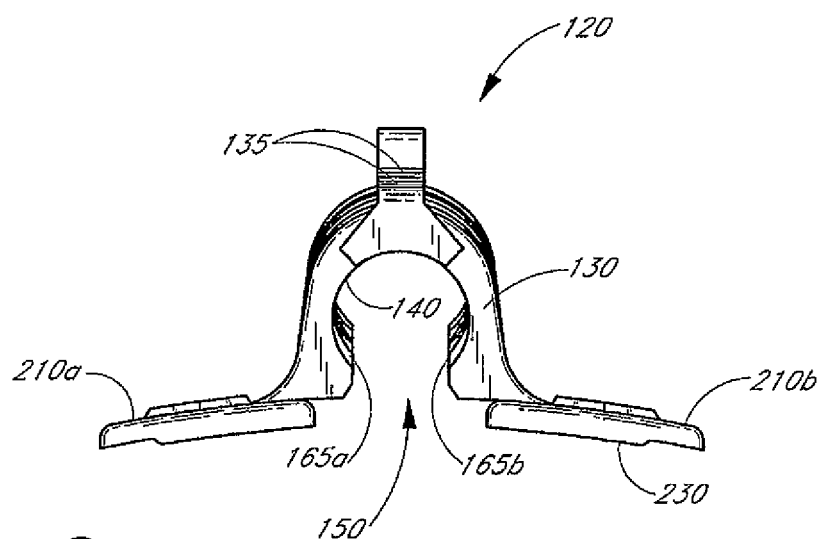
FIG. 3 is a front side view of the retainer of FIG. 2.

An embodiment of the retainer 120 is described with reference to FIGS. 2-4. FIG. 2 is a top plan view of the retainer 120 which arrests movement of the connector fitting in the longitudinal, lateral and transverse directions. FIG. 3 is a front side view of the retainer 120 from FIG. 2 and illustrates a body member 130 and footings/side mounting wings 210(*a*), 210(*b*) that extend in lateral directions from either side of the body member. The body member 130 comprises one or more curved ribs 280 spaced apart from each other along the longitudinal axis. It is advantageous for the ribs 280 of the body member 130 to be spaced sufficiently apart along the longitudinal axis so as to provide stability to the retained portion of the medical article along its length. Alternatively, the body member 130 may include a single rib 280 that has a sufficient width in the longitudinal direction to provide stability to the medical article. In this way, the longitudinal length of the retained portion is sufficient to inhibit the rocking of the medical article within the retainer 120. Also, the lateral dimension of the body member 130 of the retainer desirably allows the healthcare provider to easily and naturally grip the body member.

With reference to FIG. 3, the inside surfaces of the ribs 280 or body member 130 face towards the patient's skin when in use and generally define an inverted central channel 140. The channel 140 may be defined by a body member 130 having a single rib 280 or a plurality of ribs 280. The inverted channel 140 extends on the underside of the body member 130 in a longitudinal direction for receiving a section of the connector fitting in the illustrated embodiment.

The inner surfaces of the ribs 280 are capable of receiving a portion or length of the medical article and are generally configured to house, to preferably grip, and to secure this portion of the medical article. In the illustrated embodiment, the inner surfaces of the ribs 280 have a generally semi-circular cross-sectional shape. An inner surface contour of the ribs 280 preferably is selected depending on the geometry of the portion of the medical article to be retained. For example, in a retainer 120 that is configured to retain a portion of a medical article that has a constant outer diameter, the inner surfaces of the ribs 280 preferably have a constant radius along its length. In contrast, in a retainer 120 configured to retain a portion of a medical article having a tapering outer surface, the ribs 280 preferably have tapering inner surfaces and radii that vary along the longitudinal axis. Additional embodiments of the inner surfaces of the ribs 280 or central channel 140 of the retainer can comprise a plurality of different radii and/or tapering regions. For example, as illustrated in FIGS. 1-5, the inner surfaces of the ribs 280 or channel 140 have a generally constant cross-sectional shape (e.g., a generally constant diameter to cooperate with a tubular connector fitting body). Thus, the body member 130 of the retainer 120 illustrated in FIGS. 1-5 preferably is configured to retain a portion of a medical article that has a generally constant outer radius along its length.

In this way, the size and shape of the central channel 140 can be chosen to match or to approximate the size and shape of the medical article or portion thereof, e.g., the connector fitting, to be retained. By matching the inner surface contour of the central channel 140 to the outer surface of the secured portion of a medical article, a more effective securement may be achieved. In addition or in the alternative effective securement can also be achieved by the engagement of one or more abutment surfaces of the retainer with one or more contact surfaces on the medical article. In certain embodiments, an abutment surface of the retainer is located on or between the distal and proximal ends of the spin nut. A contact surface on the medical article corresponds to the abutment surface on the retainer when the medical article is placed within the retainer. Each abutment surface can cooperate with a contact surface on the medical article to inhibit movement of the medical article relative to the retainer. Exemplary abutment surfaces and contact surfaces are described below.

Although the inner surfaces of the ribs 280 or central channel 140 can be formed in various shapes depending upon the desired application (e.g., depending upon a shape of the retained portion of the medical article for which the retainer is designed to be used), the inner surfaces are desirably spaced a sufficient length in the longitudinal direction to stabilize the connector fitting, catheter hub, or other medical article, rather than act as a fulcrum for the fitting, as mentioned above. That is, the retainer 120 receives a sufficient length of the connector fitting to inhibit movement of the fitting in the lateral, longitudinal and transverse direction (i.e., to inhibit yaw, pitch and axial movement of the article).

As shown most clearly in FIG. 3, the lower side of the retainer 120 includes an access or lower opening 150. In some embodiments, the lower opening 150 has generally parallel sides along the longitudinal axis to match generally the shape of the medical article. In other embodiments, the lower opening 150 has generally tapering sides to match generally the shape of the medical article. The lower opening 150 may include contouring (e.g., chamfers) along its periphery in order to guide the medical article into the central channel 140 when inserting the medical article into the retainer 120.

The illustrated retainer 120 further comprises at least one retention surface 165(a), 165(b) disposed on a lower side of the inners surfaces of the ribs 280 or inverted channel 140. The retention surface holds at least a portion of the retained medical article within the channel 140 and hence away from the patient's skin. This support can be provided by, for example, an adhesive, a region of the inverted channel which provides a degree of snap-fit with the retained medical article, two or more ribs 280 of the inverted channel which provide a degree of snap-fit with the retained medical article, or a combination of the adhesive and a region of snap-fit. The adhesive can be located on one or more surfaces of the retainer 120 that contact the medical article. For example, the adhesive could be located on the inner surface of the ribs 280 or on an abutment.

As shown most clearly in FIG. 3, the present embodiment of the retainer 120 includes multiple pairs of retention surfaces 165(a), 165(b). The corresponding retention surfaces 165(a), 165(b) of each pair lie on opposite sides of the access opening 150 from each other. In this embodiment, the retention surface 165(a) is a portion of the surface that defines the central channel 140 and is located on the lower side of the central channel 140. The retention surface 165(a) is located to one side of the central axis. The other retention surface 165(b) is a portion of the surface that defines the central channel 140 and is located on the lower side of the central channel 140. The retention surface 165(b) is further located to the side of the central axis that is opposite to the retention surface 165(a). Once the medical article is placed in the central channel 140, the retention surfaces 165(a), 165(b) each hold a portion of the retained section of the article within the channel 140. While multiple retention surfaces are illustrated in FIG. 3, either retention surface 165(a); (b) can be individually employed in variations of the present retainer and still support the medical article within the channel 140.

Pressure can be provided by the retention surfaces 165 which hold the medical article within the retainer 120 in the illustrated embodiment. The retention surfaces 165 provide a degree of snap fit between the retainer 120 and the medical article. The degree of snap-fit can be increased by extending the inside of the one or more ribs 280 or central channel 140 through an arc of greater than 180°. As shown most clearly in FIG. 3, in one embodiment the arc extends for more than 180 degrees in order to more firmly support the retained portion of the medical article. In the illustrated embodiment, the walls of the central channel 140 extend through an arc of approximately 270°. The length of such an arc provides a snap-fit securement between the central channel 140 of the body member 130 and the secured portion of the medical article. In this way, the medical article can be placed in position prior to attaching the securement device 100 to the patient without concern that the medical article will shift while the healthcare provider is attaching the device 100 to the patient. Additionally, the releasable engagement provided by a snap-fit connection also permits the retained portion of the medical article to be readily released from the retainer 120.

The retainer 120 can include a generally rigid structure (at least in comparison to foam or tape) and is principally defined by the body member 130 and the mounting wings 210(a), 210(b). The body member 130 further includes a spine 145 which extends in a proximal direction from the body member 130. The body member 130, however, preferably is somewhat flexible in nature, due both in-part to its structure and to the material used to form the body member 130. Suitably rigid but flexible materials include, for example, but without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. However, other materials can be utilized.

In the embodiment illustrated in FIGS. 1-5, the body member 130, including the spine 145, and mounting wings 210(a), 210(b) are integrally formed to comprise a unitary retainer. This can be accomplished in any of a variety of ways well known to those skilled in the art. For instance, the entire retainer can be injection molded in order to reduce fabrication costs. The illustrated retainer 120 preferably is formed by injection molding using polyethylene or polypropylene material. The retainer, however, can comprise a non-unitary body member 130, spine 145, and/or mounting wings 210(a), 210(b). In this manner, the body member, the spine, and one or both of the mounting wings is formed separately and then coupled together. Additionally, the body member 130, the spine 145, and mounting wings can have other forms and can have other orientations relative to one another. For example, the spine 145 can be made from a stiff but somewhat flexible plastic so as to allow the spine 145 to be moved in a radially direction to ease ingress/egress of the medical article to be retained. The body member 130 also can be clear or transparent to facilitate alignment of the retainer 120 with the connector fitting or other medical article during installation.

Each mounting wing 210(a), 210(b) preferably comprises a glue dam around a portion of its periphery on its underside. The glue darn restricts adhesive flow beyond an inner edge of the respective mounting wing. The outer edge of each mounting wing 210(a), 210(b) does not include the glue dam (as best seen in FIGS. 3 and 4) to allow any excess glue or adhesive to seep out from under the mounting wing during the manufacturing process in the lateral direction away from the retainer 120.

The body member 130 of the retainer is attached to the upper surface 170 of the anchor pad 110 via the mounting wings 210(a), 210(b), as is shown in FIG. 1. The body member is desirably secured to the upper surface of the pad by a solvent bond adhesive, such as cyanoacrylate or other bonding material. One such adhesive is available commercially as Part No. 4693 from 3M.

When the anchor pads 110 are secured to the skin of the patient; the medical article is inhibited from moving substantially in either the lateral or transverse directions relative to the patient. Longitudinal movement of the medical article is inhibited by engagement between at least one abutment surface on the retainer 120 and a contact surface or mating surface on the medical article. The abutment surface on the retainer 120 preferably extends generally normal to the axis of the central channel 140. The abutment surface can be located along the longitudinal axis of the retainer. For example, the abutment surface can be located on a distal side or clip 147 of the spine 145, the proximal 127 or distal 125 ends of the retainer body 130, or between the proximal and distal ends of the retainer at a location of a step or radii change. In the illustrated embodiment, spine 145 extends beyond the proximal end 127 of the retainer 120. Moreover, multiple abutment surfaces on the retainer 120 can be employed with each abutment surface being the same or a different type of abutment surface. In other arrangements, the spine 145 extends from one or both of the mounting feet 210(a), 210(b). When the spine 145 attaches to the mounting feet 210 which are located proximal to the retainer body 130, the longitudinal length of the spine is less than when the spine is attached to the retainer body 130.

Alternatively, the spine 145 or abutment surface attaches at two locations to the retainer 120 and forms a loop there between. For example, one end of the loop is attached to one mounting foot 210(a), while the other end of the loop is attached to the other mounting foot 210(b). The portion of the loop located between the mounting feet 210 loops over the top of the spin nut so that a portion of the loop is located on the proximal side of the spin nut to thereby inhibit motion of the spin nut in a proximal direction.

The retainer 120 thus preferably includes one or more abutment surfaces. In the illustrated embodiment, the retainer further includes multiple abutment surfaces that are formed by one or more ribs 280 in the body member 130. In the form of a rib 280, one abutment surface forms one side of the rib and another abutment surface forms the other side of the rib 280. The ribs 280 connect the mounting wings 210(a), 210(b) to the ridge 137. The ribs 280 provide additional surfaces for the healthcare provider to grip the retainer 120. Multiple abutment surfaces allow the medical device to be retained in multiple positions relative to the retainer. Located between the one or more ribs 280 are slots 220.

To arrest longitudinal motion in the illustrated embodiment, two contact surfaces in the form of a single radially extending member or spin nut are employed on the medical article. With the connector fitting installed in the channel 140, the spin nut extends between the distal side of the clip 147 of the spine 145 and the proximal side 127 of the proximal most rib 280 to inhibit longitudinal motion of the medical article in both longitudinal directions. The contact between these two abutment surfaces on the retainer and their corresponding contact surfaces on the medical article arrests motion in the longitudinal direction.

As shown in FIG. 2, the retainer 120 includes at least one spine 145 that forms an abutment surface. The proximal end of the spine 145 curves downwardly and includes a fork-shaped clip 147 adapted to straddle the radially extending member on both sides of the longitudinal axis. The clip 147 preferably has a curved circular shape about the longitudinal axis that extends less than 180 degree, such as 45 degrees to 90 degrees. This curved shape enables the clip 147 to slip over an edge of the spin nut but yet not interfere with the outer diameter of the catheter hub 430. Multiple spines 145 can be located circumferentially about at least a portion of the axis of the central channel 140. The distal sides of the clips 147 are spaced from the proximal end 127 of the retainer to accept the spin nut of the retained medical article there between.

The radially extending portion of the medical article is preferably in the form of a spin nut. An embodiment of a spin nut is described with reference to FIG. 5. In particular, it can be desirable for the longitudinal length between the clip 147 and the proximal end 127 of the most proximal rib 280 or body member 130 to be sufficient to receive the spin nut of the medical article therebetween; however, this distance can be slightly larger than the spin nut's thickness (as measured in the longitudinal direction) and a gap can exist between one or both sides of the spin nut and the corresponding abutment surfaces into which the spin nut has been inserted. In a preferred form, the longitudinal length between the clip 147 and the proximal end of the retainer body preferably is about five thousandths of an inch (0.005 inch, 0.127 mm) larger than the radially extending member (e.g., the spin nut). Such an arrangement can be desirable to minimize longitudinal movement of the retained portion (e.g., the spin nut in FIG. 5) of the medical article. Accordingly, a small gap can exist between any abutment surface and a corresponding contact surface before the medical article is shifted relative to the retainer 120. Once shifted, however, further longitudinal movement is prevented by the interference between the contact surface and the abutment surface.

For embodiments with multiple spines 145, those of skill in the art will recognize that each clip 147 need not have identical radial extent towards the longitudinal axis. Further, the radial location of each spine 145 need not be uniform about the axis of the central channel 140.

The inner edge of the clip 147 which faces the retainer body 130 can be chamfered (not shown) so as to ease the insertion of a radially extending member. By having the edge of the clip 147 chamfered, it becomes easier to move a radially extending member into the space between the clip 147 and the proximal end 127 of the retainer body even if the initial alignment between the space and the center of the radially extending member is not exact. The use of a chamfered edge on the clip 147 allows for a medical article to be placed into the central channel of the retainer 120 with only coarse alignment with the axis of the central channel. The alignment process is further facilitated when a portion of the retainer 120 is transparent.

Figure 4:
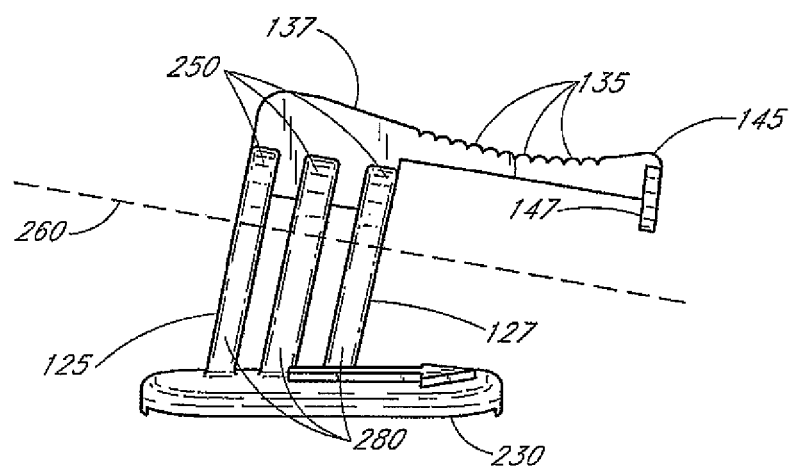
FIG. 4 is a side view of the retainer of FIG. 2.

As shown most clearly in FIG. 4, a proximal section of the spine 145 comprises one or more grooves 135 which form a grip region that a healthcare provider can press down upon. The grooves 135 enhance the friction between a finger of the healthcare provider and the spine 145. The grooves 135 encourage the finger to push down on the spine 145 to ensure that the clip 147 engages with the contact surface of the medical article.

A distal section of the spine 145 comprises a ridge 137 which forms a finger pad that a healthcare provider can press down upon. In the illustrated embodiment, the top surface of the ridge 137 is located above the adjacent surfaces of the ribs 280 but need not be. However, the ridge 137 encourages the finger to push down on the retainer 120 and discourages the healthcare provided from gripping the retainer 120 on its sides during application. Such a side grip could squeeze or constrict the retainer 120 and make it harder to slip the retainer 120 over the medical article. By pushing down on the retainer 120, this constrictive effect is avoided.

As illustrated in FIG. 3, a base surface 230 of the retainer 120 can have a concave curved shape when viewed from the front and rear sides. The degree of curvature can be varied depending on the expected location of usage or application of the securement device 100. It will be appreciated that many common sites for insertion of medical lines which require securement will be located on anatomical regions exhibiting convex curvature, such as a dorsal side of a hand, a arm, a leg, a contact surface, etc. By providing a concave bottom profile to the retainer 120, the retainer will rock less once placed upon the patient via the anchor pads 110(a), 110(b).

FIG. 4 is a side view of the retainer 120 of FIG. 2. As illustrated in FIG. 4, an axis 260 of the central channel 140 lies at an angle with respect to the base surfaces 230 of the retainer 120. The desired angle between the medical article and the patient is created by angling the axis 260 of the central channel 140. This angle is selected in order to align the axis 260 of the channel 140 of the retainer with the desired incident angle with which the medical article is to contact the skin of the patient. A variety of different angles can be used, ranging from 0° to 45°, and more preferably from 5° to 25°. For instance for the securement of a connector fitting to an intravenous catheter, it is desirable for the angle of incidence of the catheter to the skin of the patient to be between about 7° to about 15°. For securement to arterial catheters, it is desirable for the angle of incident of the catheter to the skin of the patient to be about 12.5°. By angling the axis 260 of the channel 140 at the desired angle, which will depend upon the particular securement application (e.g., securing an arterial catheter, an intravenous catheter, etc.), the proper angle of incidence for a catheter can be maintained.

Although certain features of the retainer 120 can be specifically configured for use with a catheter connector, it will be understood by those of skill in the art that such a retainer 120 can be used with other adaptors or medical lines as well. Furthermore, the retainers described herein can be modified to more effectively cooperate with various types of connector hubs and adaptors.

Medical Articles

Figure 5:
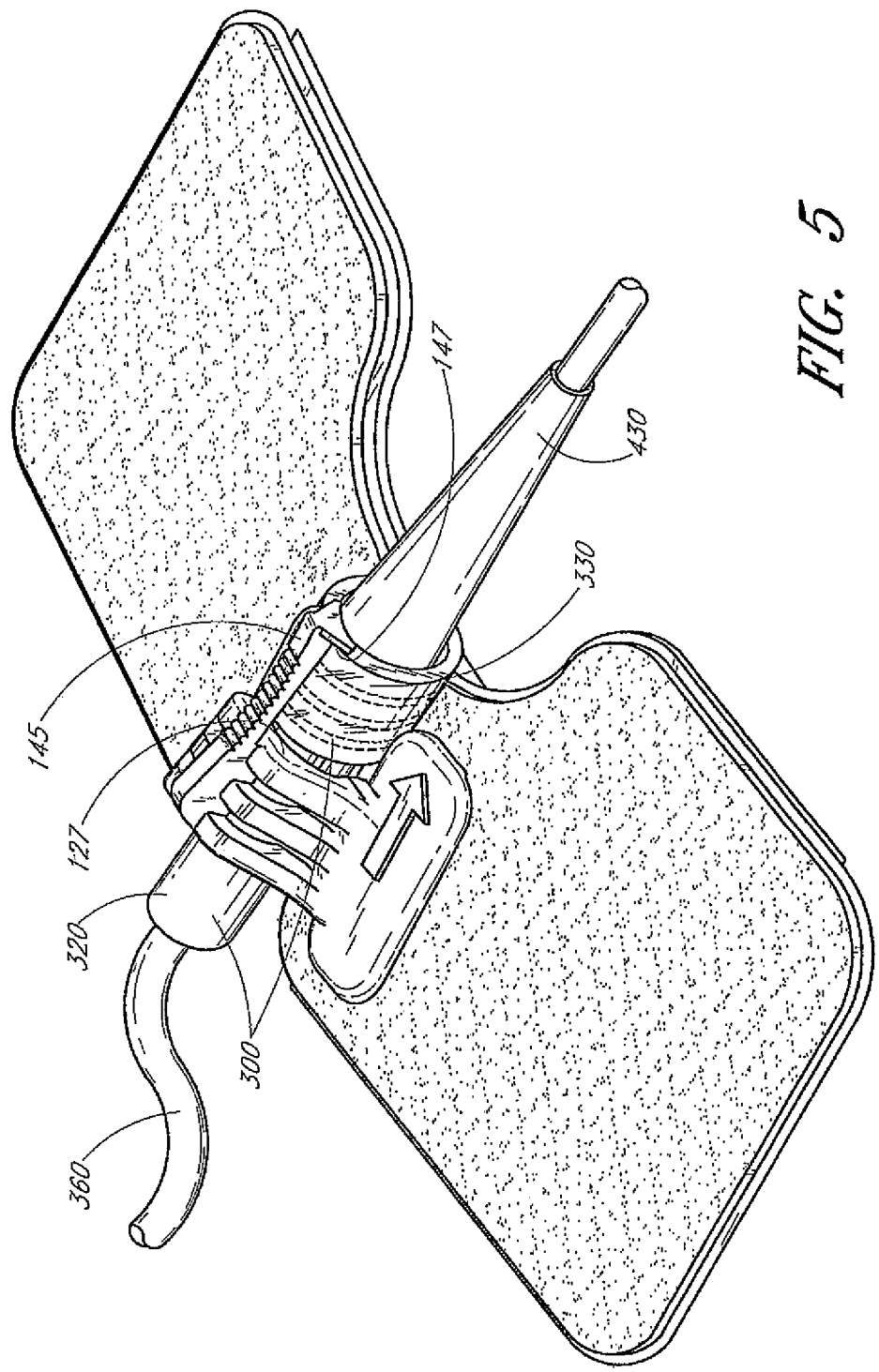
FIG. 5 is a perspective view of a connector fitting and catheter hub secured to the securement device of FIG. 1.

An exemplary medical article for use with the embodiment of the securement device described above will now be described with reference to FIG. 5. The medical article can be a single medical article or a combination of one or more medical articles. Such medical articles can be or include, for example, but without limitation, connector fittings, catheters, catheter hubs, catheter adaptors, fluid supply lines, or other similar articles. FIG. 5 is a perspective view of a catheter hub 430 and a connector fitting 300 with a spin nut 330. The connector fitting 300 is preferably disposed upon the end of a medical line 360 which can be connected to a drip bag, blood monitor, or other fluid related medical apparatus. While the retainer 120 of FIG. 2 is configured to receive a portion of the connector fitting 300, the retainer can be configured for use with the catheter hub 430.

The connector fitting 300 comprises an elongated body 320 which is attached to the end of the medical line 360. The connector fitting 300 also comprises a portion that is tapered along at least part of its longitudinal length so as to allow the end of this region to fit within the tapered conical portion of the catheter hub 430. The tapered portion of the connector fitting 300 also preferably includes a centrally disposed lumen that communicates with the lumen of the medical line.

In FIG. 5, the spin nut 330 of the connector fitting is secured in the proximal position and to the catheter hub 430. When the connector fitting 300 is inserted into the catheter hub 430, the lumen of the connector fitting is disposed in fluid communication with the lumen of the catheter hub 430. This provides fluid communication between the medical line 360 and the patient.

As seen in FIG. 5, the connector fitting 300 has at least two contact surfaces in the form of a spin nut 330 disposed upon the proximal end of the elongated body 320 of the connector fitting 300. Additional contact surfaces in the form of a second radially extending element (not shown) can also be disposed upon the elongated body 320.

The spin nut 330 is disposed upon the connector fitting 300 around the elongated body 320 of the fitting. The spin nut 330 is substantially cylindrical in form and may be fixed or movable upon the connector fitting 300. Thus, the spin nut 330 can be capable of both rotational motion around the axis of the connector fitting and axial motion in both the proximal and distal directions along the length of the elongated body 320 of the fitting. The spin nut 330 also includes internal screw threads which are illustrated with phantom lines in FIG. 5.

Still referring to FIG. 5, a catheter hub 430 includes a body that, in the illustrated embodiment, has a generally conical shape and tapers from a large radius to a smaller radius along its length. The catheter hub 430 also can include an external screw thread on the outside of the conical body near the end with the larger radius. The screw thread can be used in association with the spin nut 330 of the connector fitting 300 in order to securely interconnect the connector fitting 300 and the catheter hub 430.

The at least one abutment surface, for example spine 145, inhibits the spin nut 330 from moving in a proximal direction while the proximal end 127 of the body 130 inhibits the spin nut 330 from moving in a distal direction along the longitudinal axis. Thus, the retainer 120 at least inhibits longitudinal motion of the spin nut 330. As mentioned above, the spin nut 330 may be free to move upon the body of the connector fitting 320. However, once the spin nut 330 is coupled to the catheter adapter 430 and placed between the proximal end 127 of the body 130 and the clip 147, motion of the connector fitting 300 and the catheter hub 430 relative to the retainer 120 will be inhibited in the longitudinal direction.

Operation

An exemplary process for coupling a medical article with the securement device described above will now be described with reference to FIG. 5. A method of using the embodiment of the securement device illustrated in FIGS. 1-4 will be described in the context of starting an intravenous line. However, the aspects and features of the operational method and the use of the present securement device are not limited to this particular application.

A healthcare provider preferably begins the procedure by inserting an IV catheter into patient's vein in a known manner and then attaching an intravenous line to the IV catheter though the luer connection. In particular, the healthcare provider inserts the tapered or luer end of the connector fitting 300 into the catheter hub 430 and then turns the spin nut 330 to thread the spin nut 330 over a thread flange disposed at the distal end of the catheter hub 430. This action draws together the two medical article components and releasably interlocks them. The immediate connection of the IV line to the catheter inhibits a back flow of blood through the catheter. The healthcare provider now preferably secures the connector fitting in place on the patient using the securement device 100. In some variations of this method, however, the securement device 100 can be first be attached to one or both of the medical articles (as well as the possibly to the patient) before the healthcare provider makes the connection between the two medical articles.

FIG. 5 is a perspective view of the connector fitting 300 secured to the catheter hub 430 with the connector fitting being inserted into the retainer 120. The lower opening 150 in the retainer 120 is pressed over the connector fitting 300 whereby the elongated body of the connector fitting slides into the central channel 140 of the body member 130. Depending on the diameter of the elongated body 320, the retention surface 165 can provide a snap-fit connection between the connector fitting and the body member 130. The contact surfaces of the connector fitting preferably form one or more radially extending members (e.g., a spin nut 330), as shown in the illustrated embodiment.

Alternatively, the connector fitting is inserted in a distal direction along the longitudinal axis and into the central channel 140 of the retainer 120. The healthcare provider bends the spine 145 away from the longitudinal axis to allow the spin nut 330 to pass by the clip 147 of the retainer 120.

The radially extending member fits between the clip 147 and the proximal end 127 of the retainer body or rib 280. As can be seen, the spin nut 330 of the connector fitting 300 lies between these surfaces of the retainer 120. In addition, the elongated body of the connector fitting 300 generally lies within the interior of the ribs 280 or central channel 140 of the retainer. When guided through the lower opening 150 by the healthcare provider the body of the connector fitting 320 will lie within the interior of the ribs 280 or central channel 140 of the retainer 120. The abutment surface of the clip 147 and of the proximal end 127 of the retainer body will inhibit longitudinal migration of the connector fitting 300 and catheter hub 430 through the central channel 140 of the retainer 120.

Since a portion of the connector fitting 300, such as the spin nut 330, has a greater radial size than the size of the central channel 140 of the retainer 120, the spin nut 330 acts as a contact surface and inhibits axial motion in one direction through the central channel 140 of the retainer.

The combination of the top of the retainer and the interengagement between the spin nut 330 and the proximal end 127 of the retainer and the spine 145 arrest movement of the retained section of the medical line in three dimension: longitudinally, laterally and transversely.

Once the connector fitting 300 or other medical article enters the lower opening 150 of the retainer 120, the anchor pads 110(*a*), 110(*b*) are secured to the patient. The central channel 140 of the retainer surrounds an arc length of more than 180 degrees of the medical article. This inhibits any transverse or lateral motion of the medical article relative to the retainer 120. The connector fitting can be inserted into the retainer either before or after the hub is attached to the connector.

The healthcare provider can first remove one portion of the release liner 180 from the anchor pad 110 by gripping the pull tab 190 and pulling the liner 180 away from the lower surface 160 of the anchor pad 110. This exposes the adhesive layer of the anchor pad, which can then be applied to the skin of the patient near the site where the healthcare provider desires to secure the connector fitting 300 or other medical article. The adhesive layer of the second anchor pad which is located in a lateral direction from the first anchor pad can be similarly exposed. The remainder of the release liner 180 for the first and second anchor pads can then be removed and the anchor pad fully attached to the skin of the patient. As a variation, the release liner on one anchor pad can be pulled away and the anchor pad can be fully attached to the patient before attaching the second anchor pad to the patient.

As understood from the above description of the securement device embodiment shown in FIGS. 1-5, the securement device 100 arrests longitudinal movement of the retained section of the connector fitting 300 by interacting with at least one and preferably two contact surfaces of the spin nut 330, which constitutes a radially extending member in the illustrated embodiment. This approach for arresting longitudinal movement can also be used with other types of radially extending members or contacts (e.g., contact surfaces) on the connector fitting 300 or other medical articles or components thereof. For example, spine 145 can be configured to capture a tab, spline (e.g., a longitudinally extending spline) or collar on the catheter hub that is disposed on the proximal side of the spin nut 330. Additionally, the retainer can be configured to not only capture two contacts on the medical article(s) but also can be configured to receive one or more radially extending members of the medical article(s).

The spin nut 330 and the connector fitting can be manufactured individually or as a unitary member. If the inside surface contour of the retainer 120 is substantially larger than the outer diameter of the connector fitting, an annular member can be installed around the connector fitting to allow a form of snap-fit between the outer diameter of the annular member and the inside surface of the retainer.

Additionally or in the alternative to the one or more abutment surfaces or to the snap-fit engagement, at least a portion of the central channel 140 in all of the illustrated embodiments can be at least partially coated with an adhesive (e.g., an adhesive that preferably releasably holds the fitting within the retainer channel) to limit or restrict longitudinal movement. Alternatively, the medical article can include an adhesive section to hold the medical article in the channel and/or relative to the retainer.

Alternatively the elongated body or the connector 300 may incorporate one or more contact surfaces in the form of a varying outer diameter or a tapering outer surface. To engage with the tapering outer surface, the channel 140 can include one or more abutment surfaces in form of a matching tapering inner surface along its length. Additional embodiments of the central channel 140 of the retainer can comprise a plurality of different abutment surfaces in the form of radii and/or tapering regions. In this way, the size (i.e., radii, tapered) of the central channel 140 can be chosen to match or approximate the size of various standard connector fittings or portions thereof. By matching the inner surface contour of the central channel 140 to the outer surface of the connector fitting, a more effective securement may be achieved.

Figure 6:
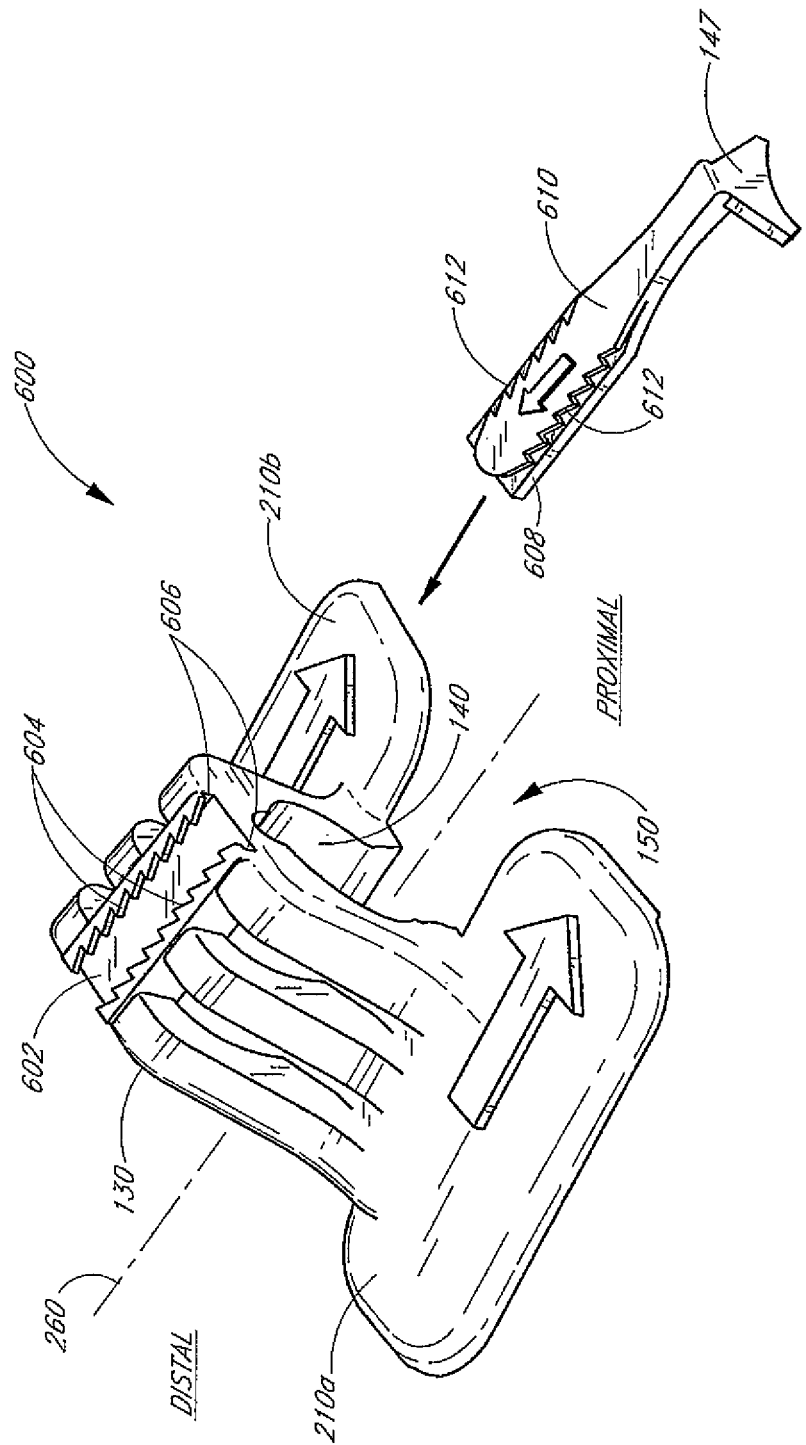
FIG. 6 is a perspective view of a second embodiment of a retainer having a movable spine and ratchet arrangement to accommodate medical devices with different longitudinal lengths.
Figure 7:
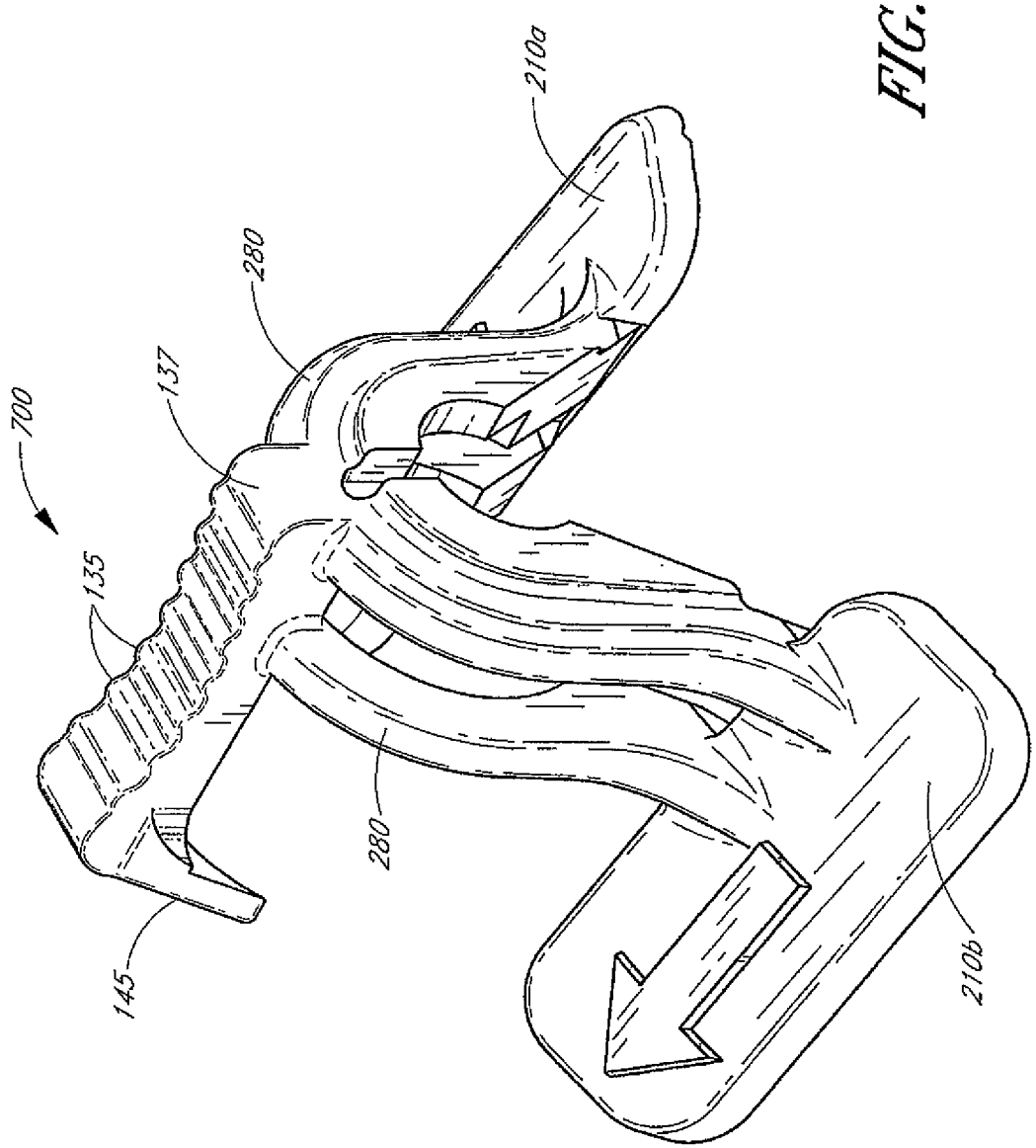
FIG. 7 is a perspective view of a third embodiment of a retainer having two abutment surfaces located between the proximal and distal ends of the retainer body.
Figure 8:
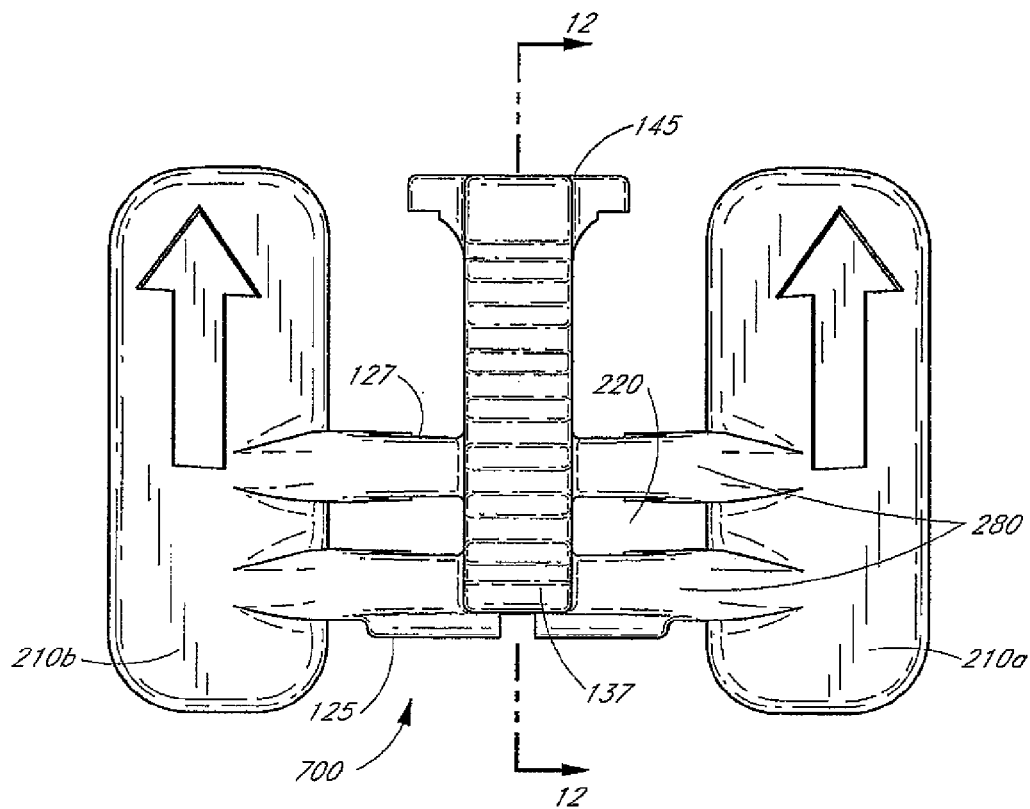
FIG. 8 is a top plan view of the retainer of FIG. 7.
Figure 9:
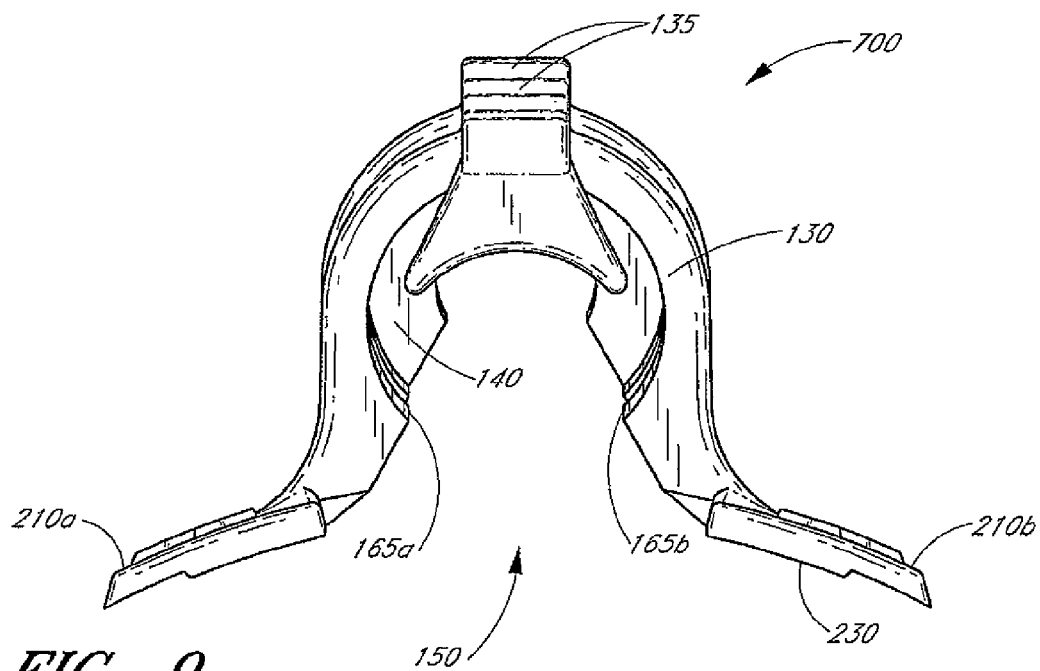
FIG. 9 is a front side view of the retainer of FIG. 7.
Figure 10:
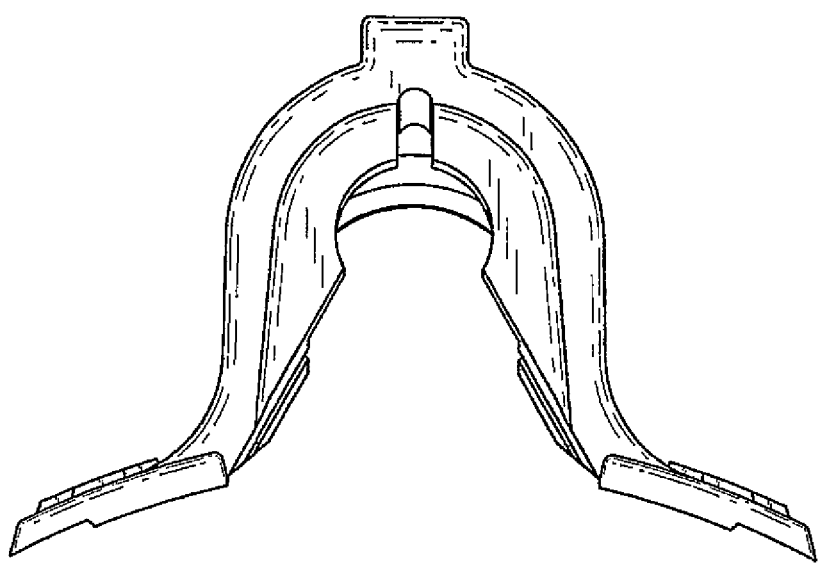
FIG. 10 is a back side view of the retainer of FIG. 7.
Figure 11:
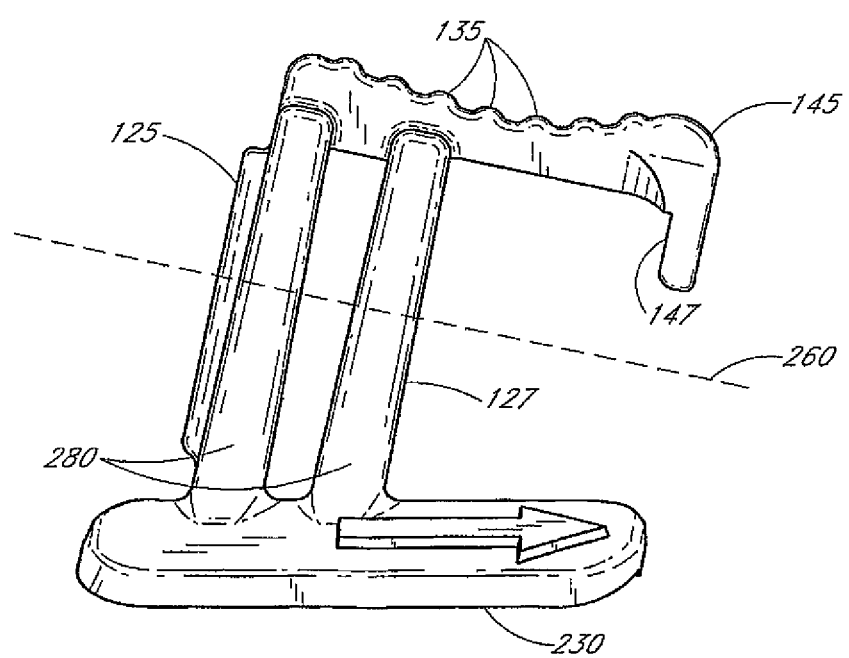
FIG. 11 is a side view of the retainer of FIG. 7.
Figure 12:
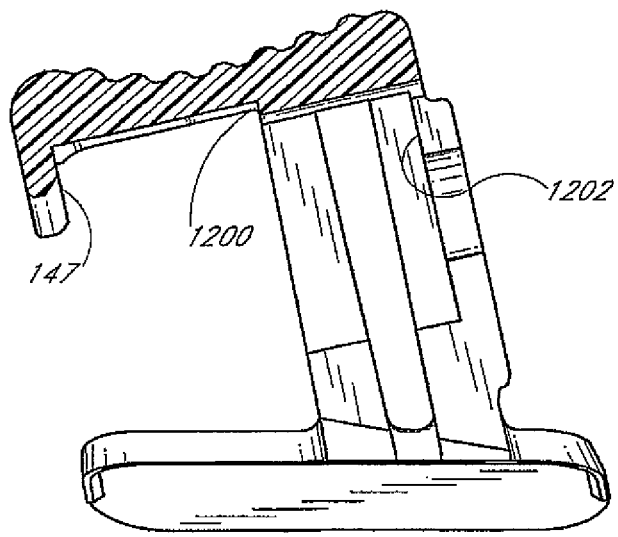
FIG. 12 is a cross section view taken along line 12-12 in FIG. 8 illustrating the abutment surfaces of the retainer.
Figure 15:
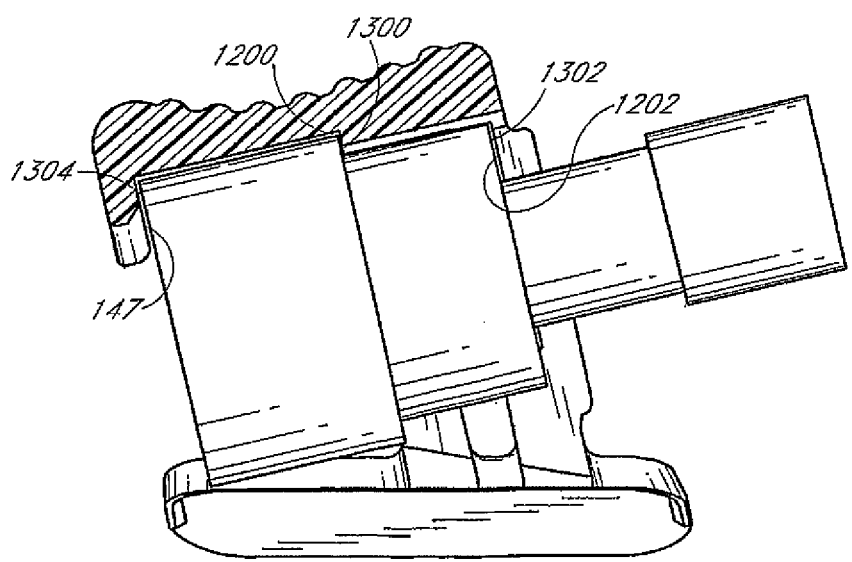
FIG. 15 is a cross section view taken along line 15-15 in FIG. 14 illustrating the abutment surfaces of the retainer in register with the contact surfaces of the medical article.
Figure 13:
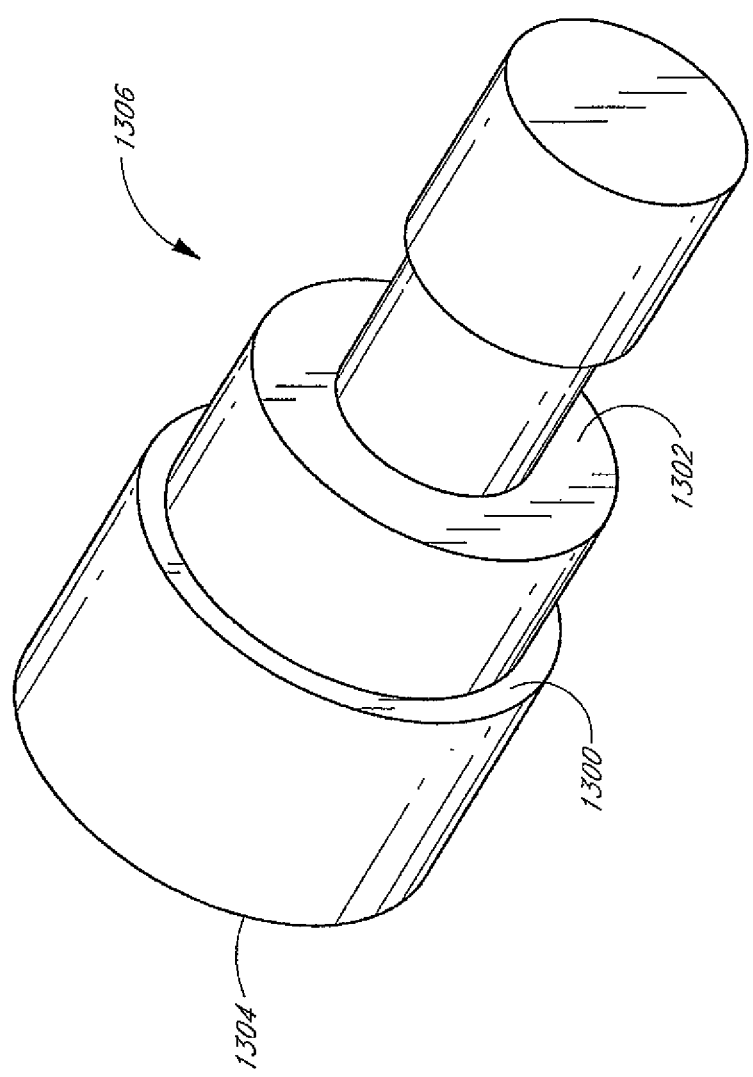
FIG. 13 is a simplified perspective view of a medical article that includes contact surfaces corresponding to the abutment surfaces illustrated in FIG. 12.
Figure 14:
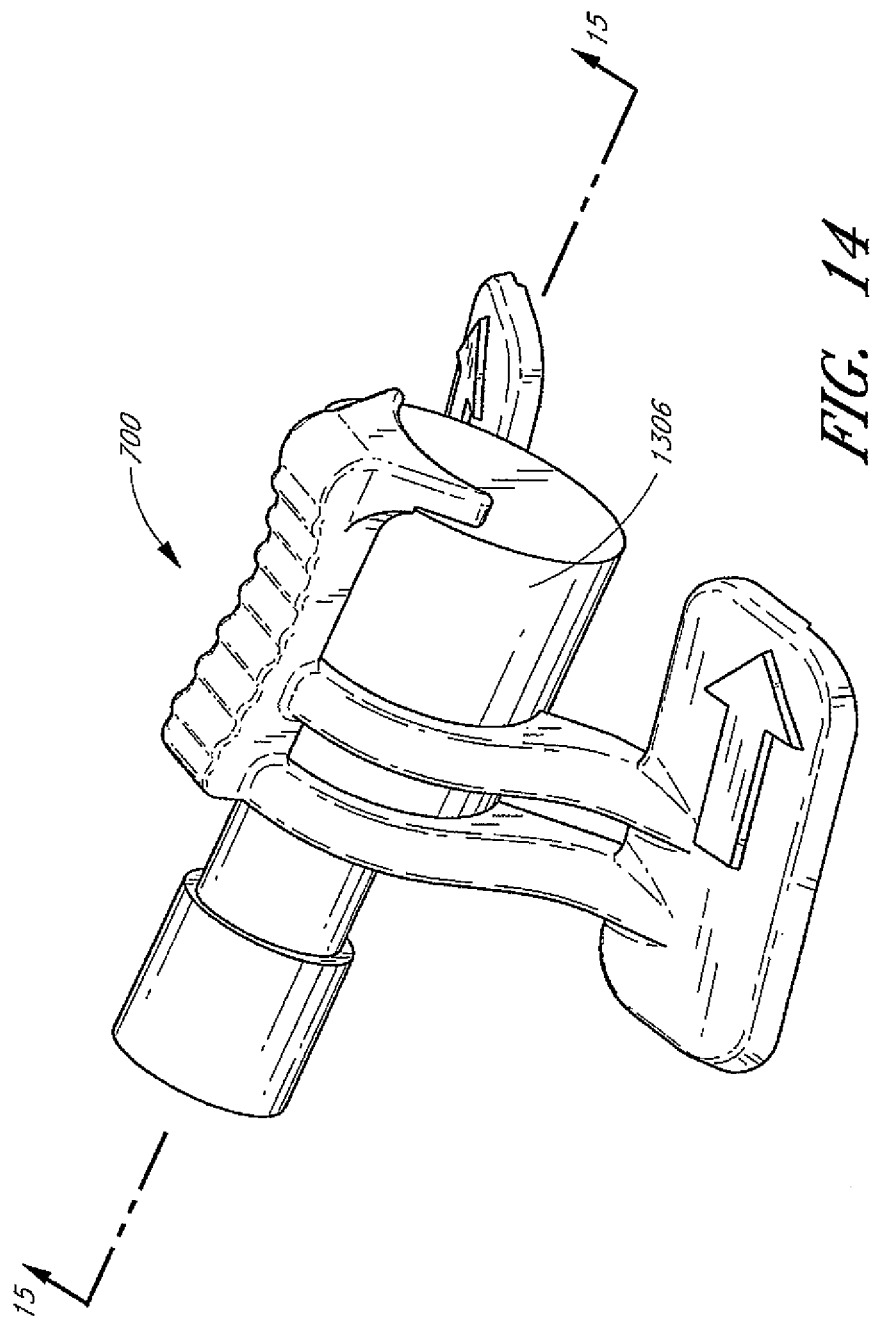
FIG. 14 is a perspective view of the medical article illustrated in FIG. 13 secured to the retainer of FIG. 7.
Figure 16:
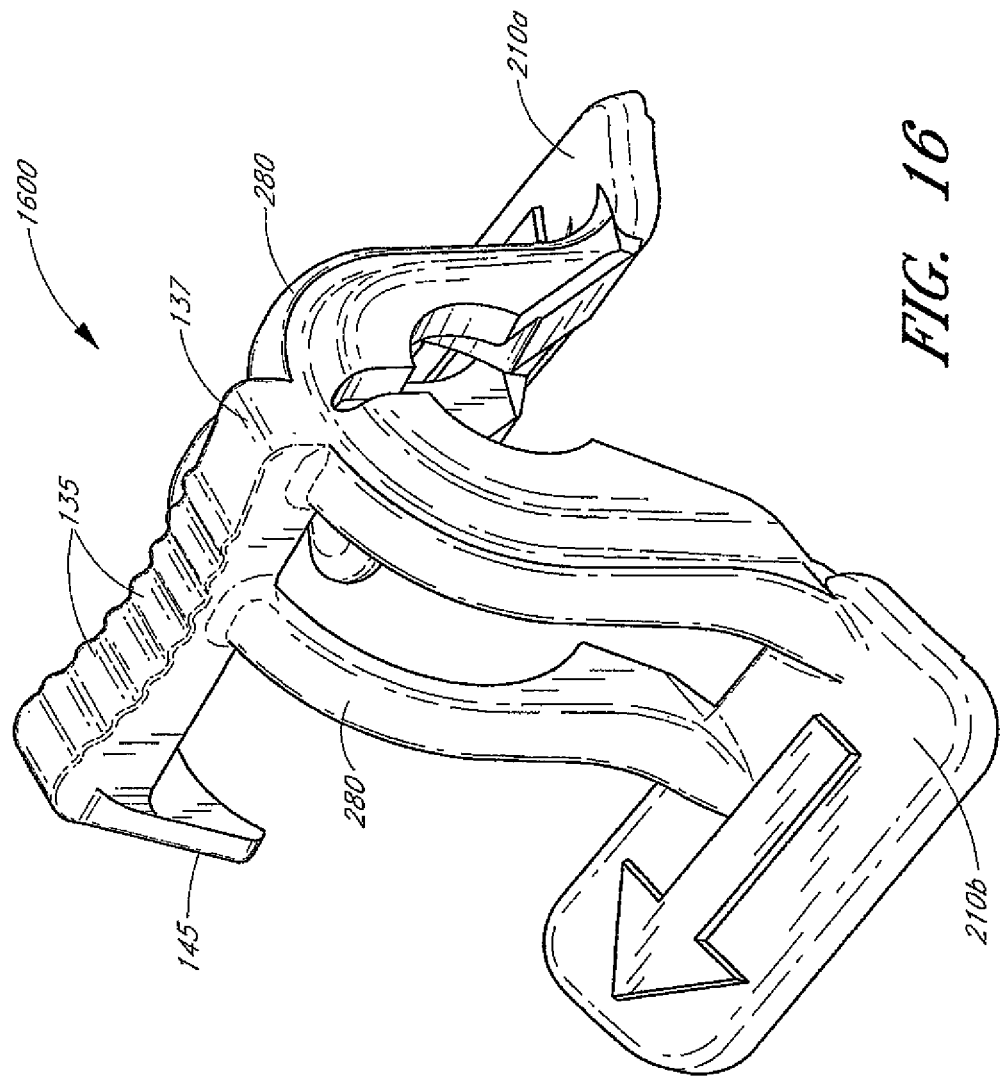
FIG. 16 is a perspective view of a fourth embodiment of a retainer having an abutment surface located between the proximal and distal ends of the retainer body.
Figure 17:
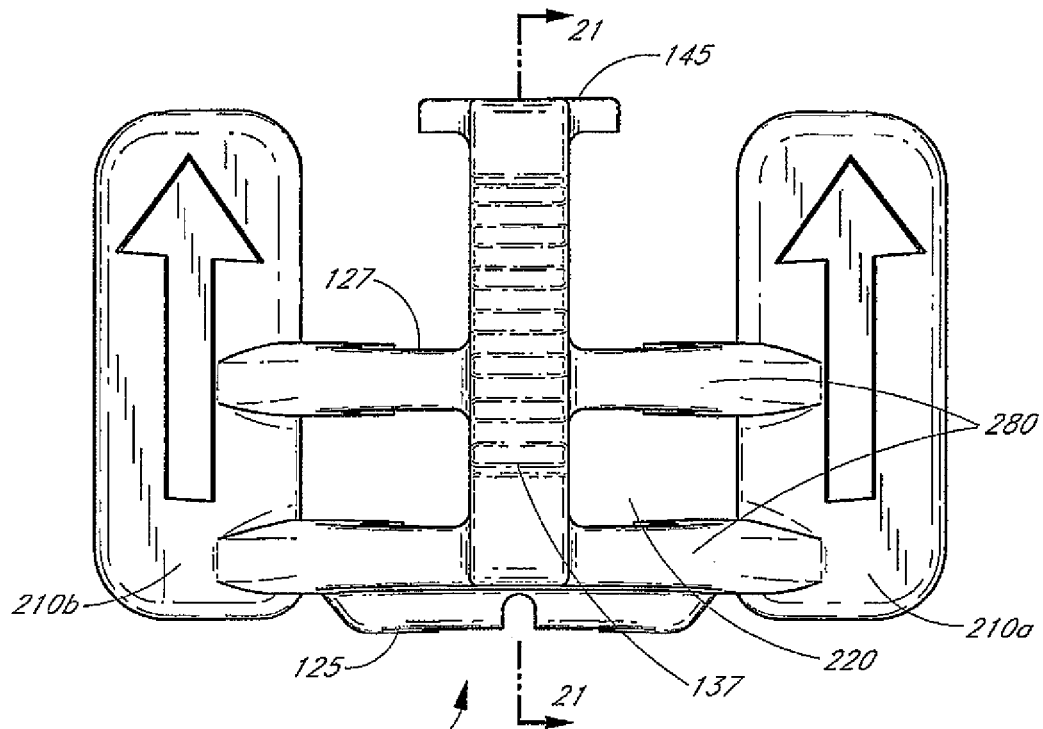
FIG. 17 is a top plan view of the retainer of FIG. 16.
Figure 18:
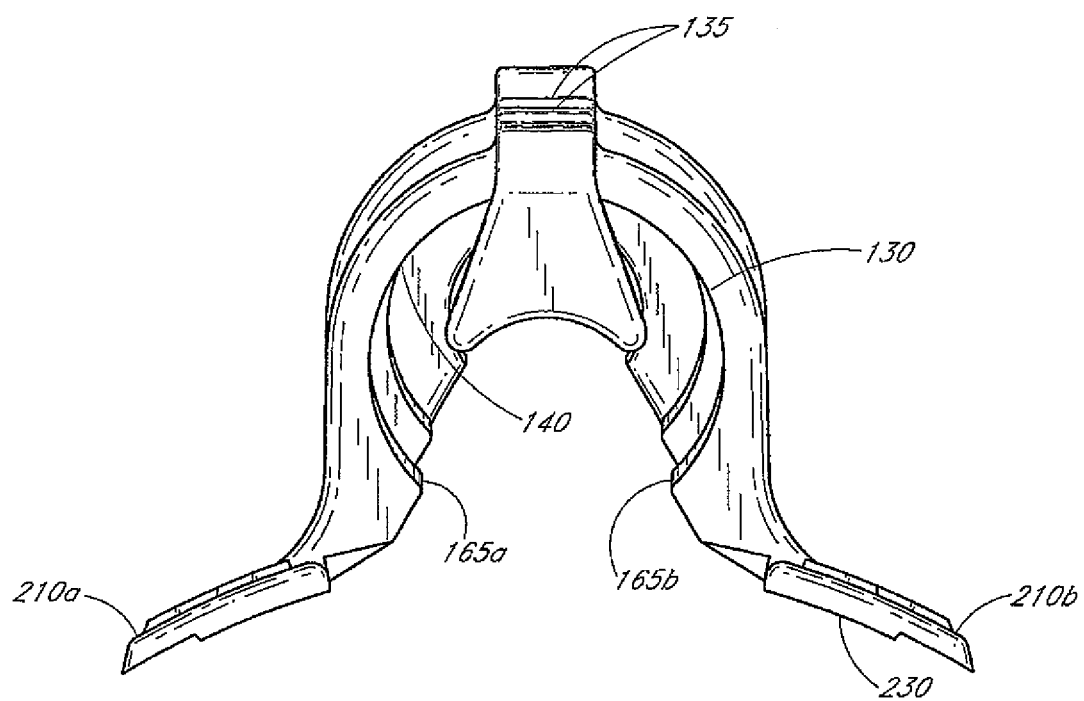
FIG. 18 is a front side view of the retainer of FIG. 16.
Figure 19:
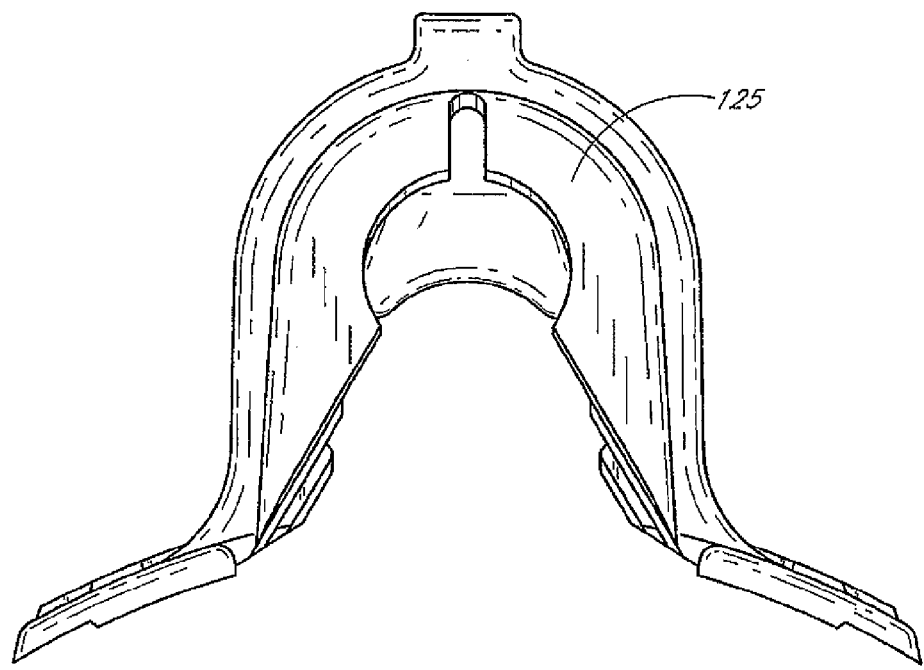
FIG. 19 is a back side view of the retainer of FIG. 16.
Figure 20:
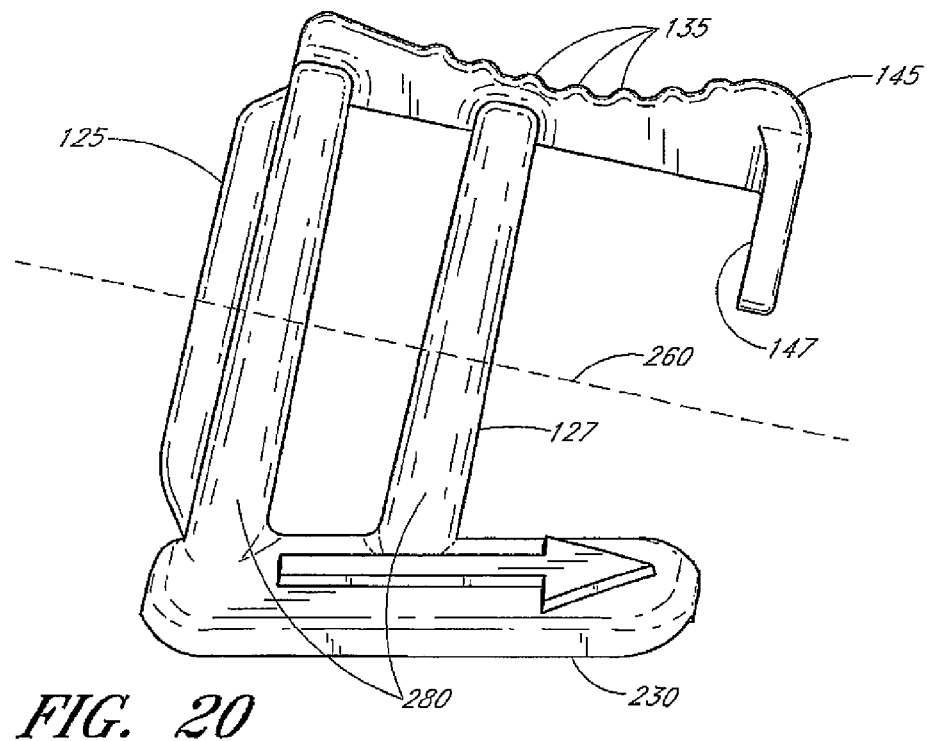
FIG. 20 is a side view of the retainer of FIG. 16.
Figure 21:
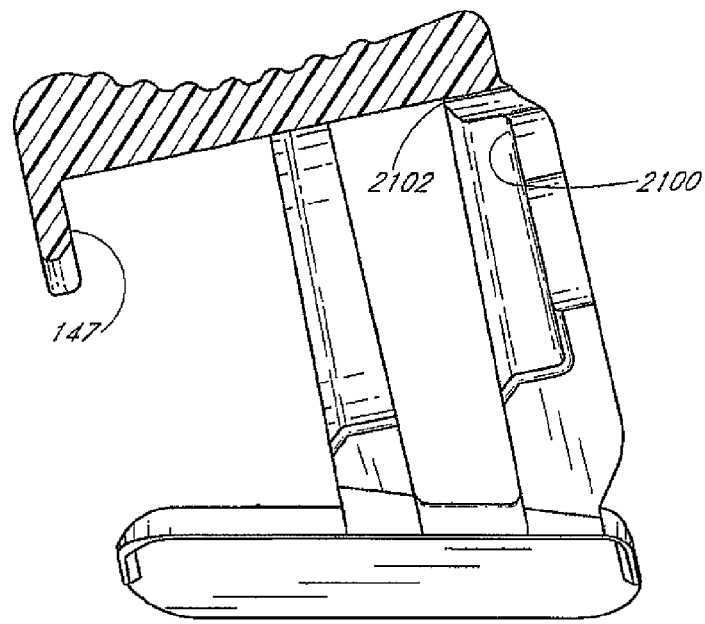
FIG. 21 is a cross section view taken along line 21-21 in FIG. 17 illustrating the abutment surface of the retainer.
Figure 24:
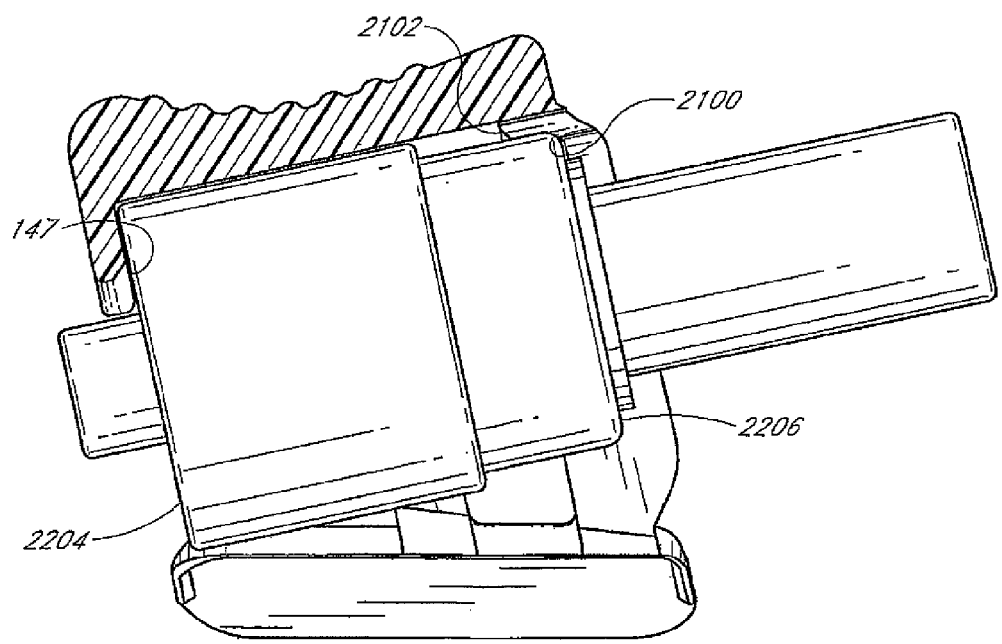
FIG. 24 is a cross section view taken along line 24-24 in FIG. 23 illustrating the abutment surface of the retainer in register with the contact surface of the medical article.
Figure 22:
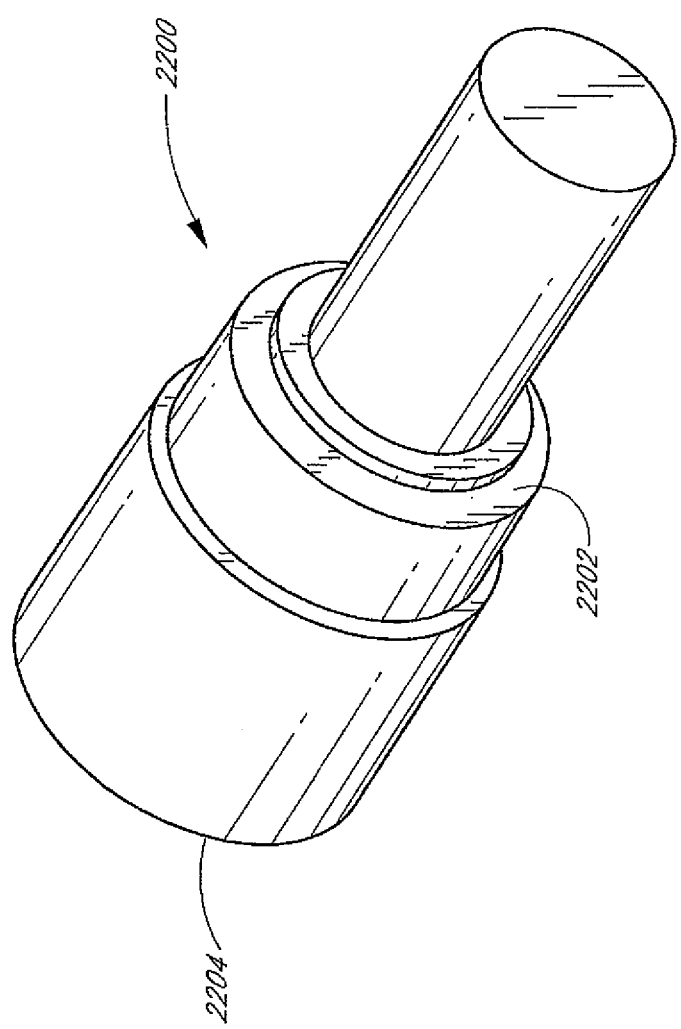
FIG. 22 is a simplified perspective view of a medical article that includes a contact surface corresponding to the abutment surface illustrated in FIG. 21.
Figure 23:
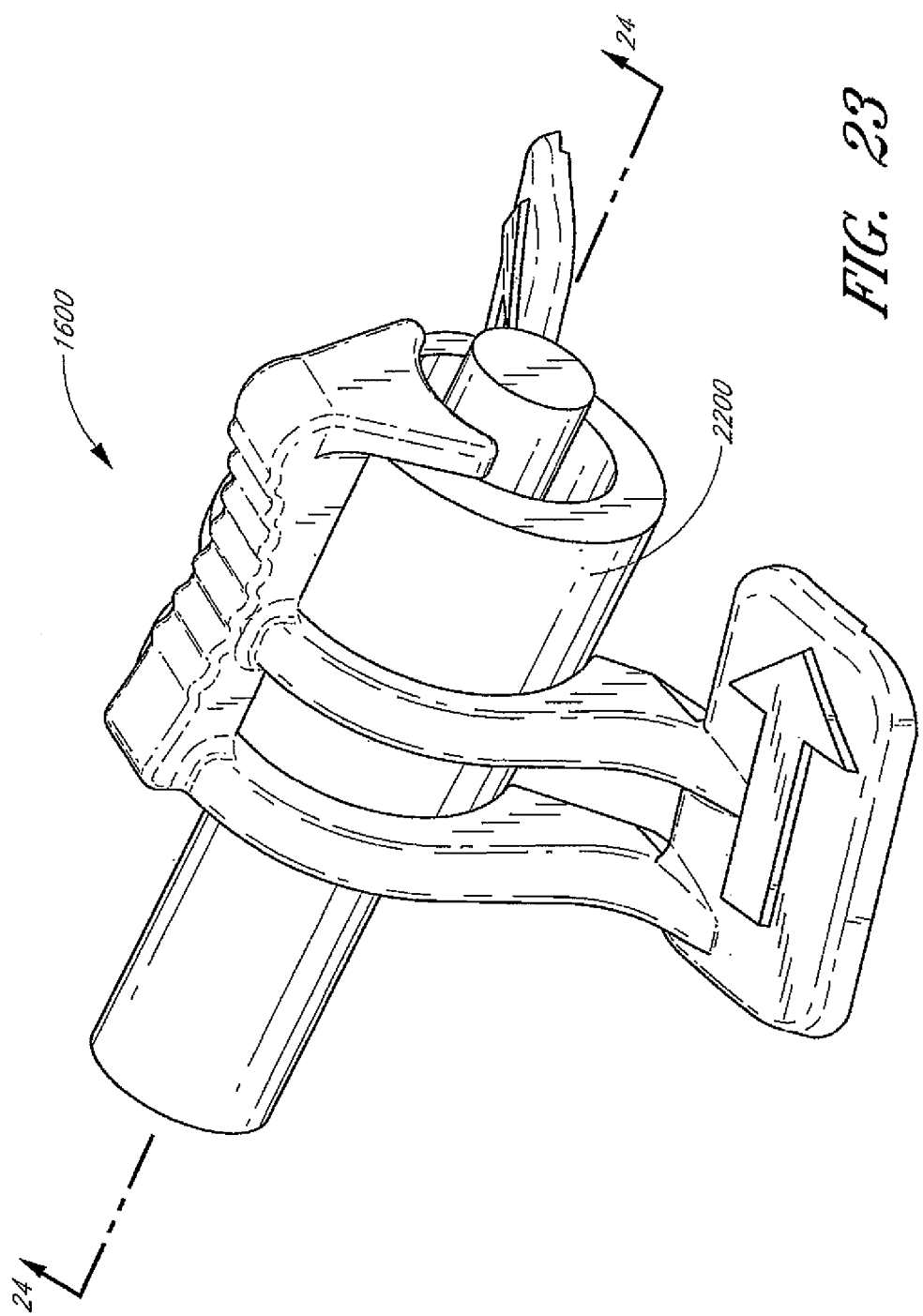
FIG. 23 is a perspective view of the medical article illustrated in FIG. 22 secured to the retainer of FIG. 16.
Figure 25:
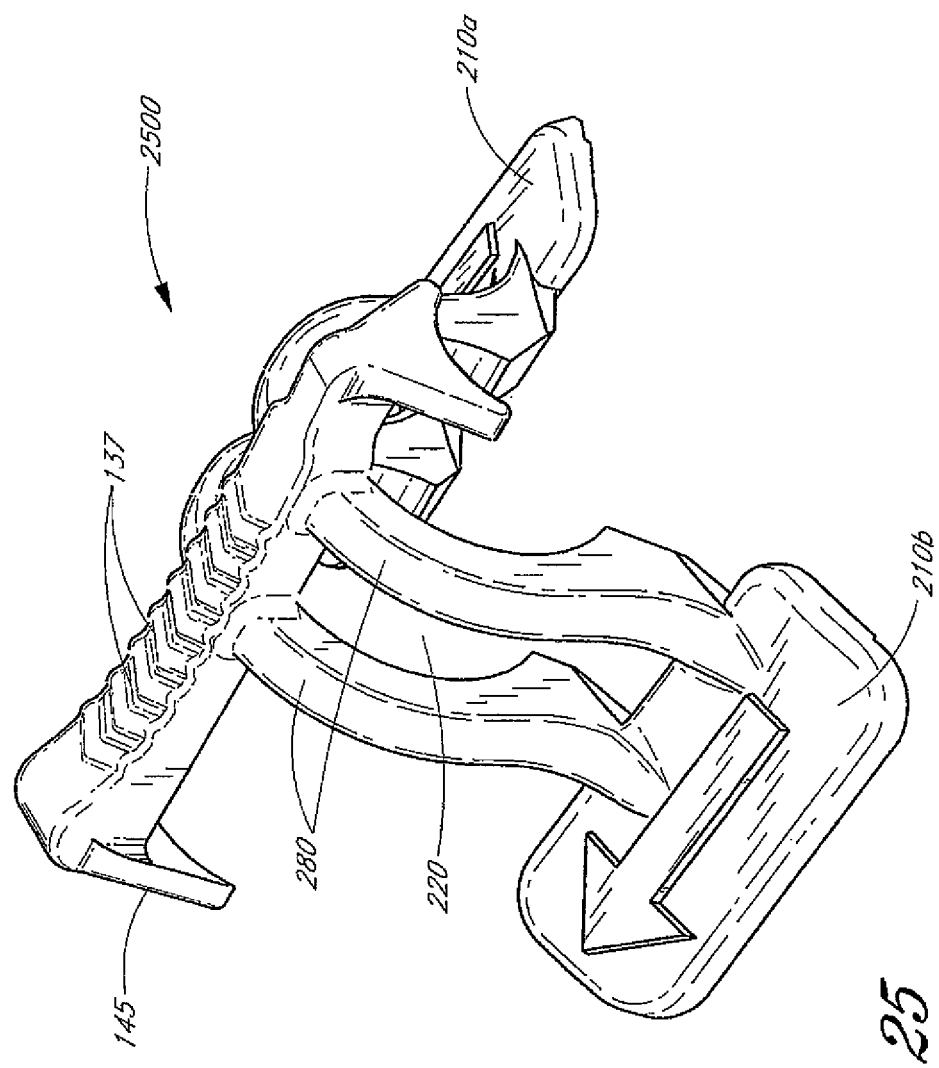
FIG. 25 is a perspective view of a fifth embodiment of a retainer having abutment surfaces located outside of the region located between the proximal and distal ends of the retainer body.
Figure 26:
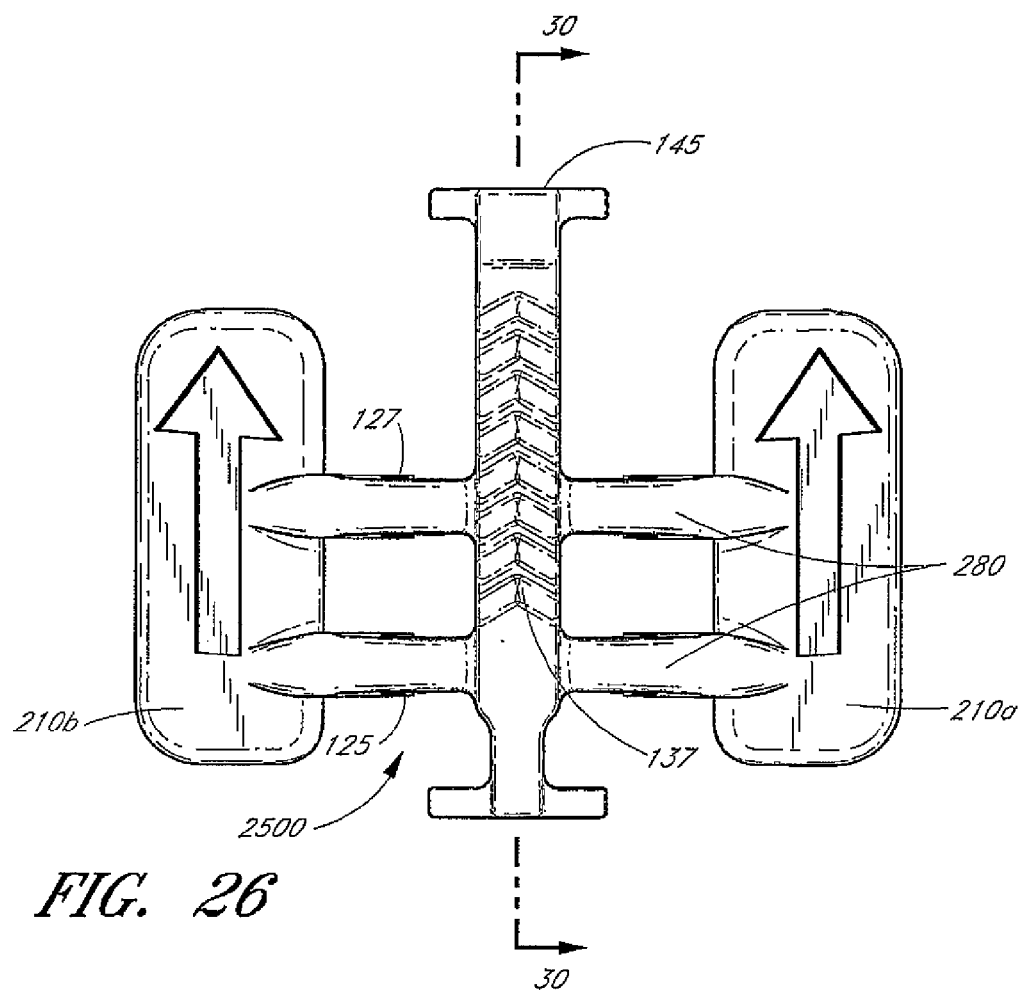
FIG. 26 is a top plan view of the retainer of FIG. 25.
Figure 27:
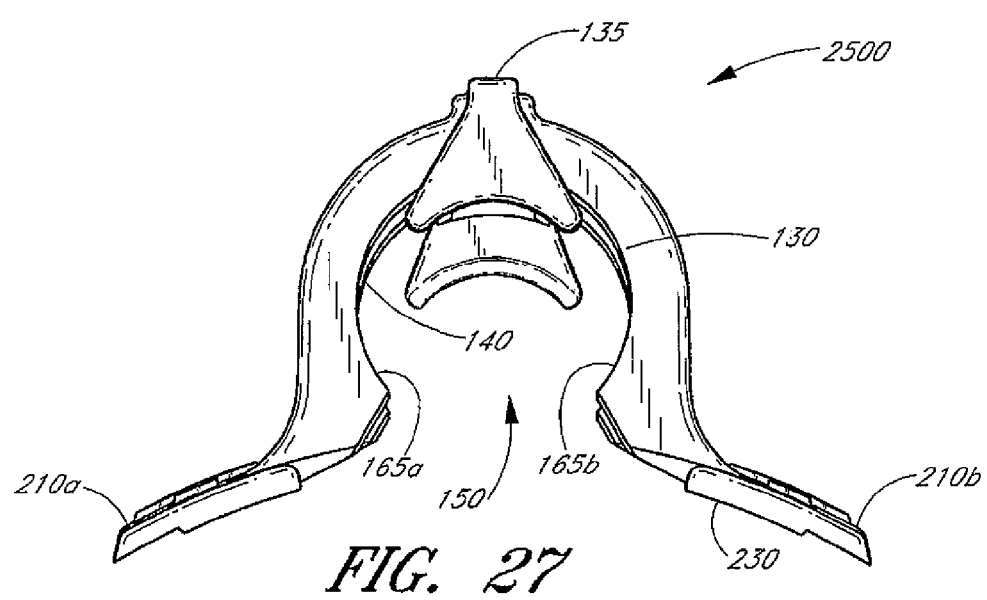
FIG. 27 is a front side view of the retainer of FIG. 25.
Figure 28:
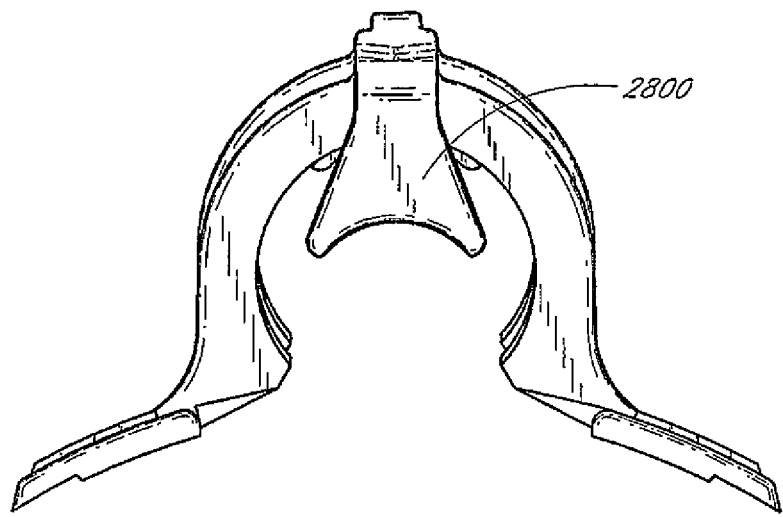
FIG. 28 is a back side view of the retainer of FIG. 25.
Figure 29:
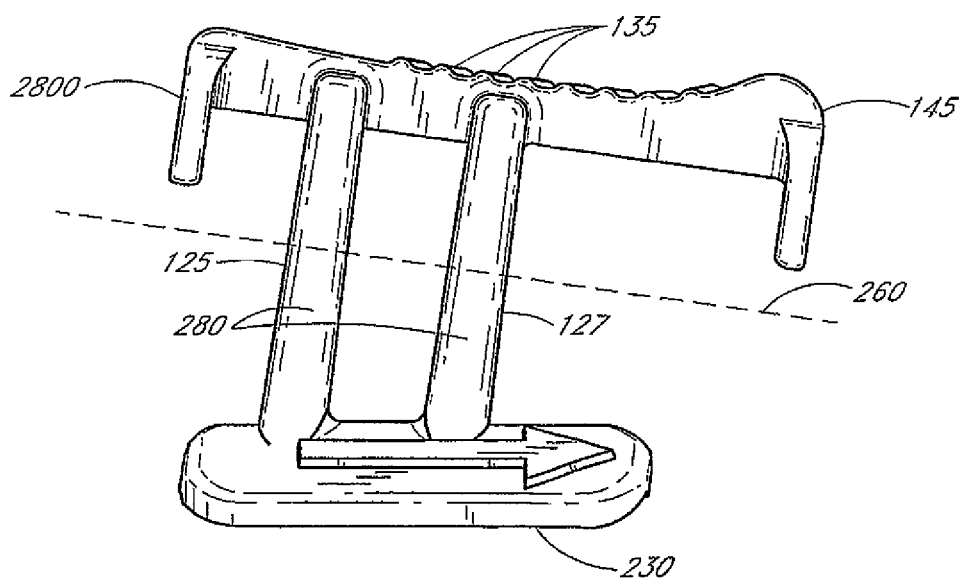
FIG. 29 is a side view of the retainer of FIG. 25.
Figure 30:
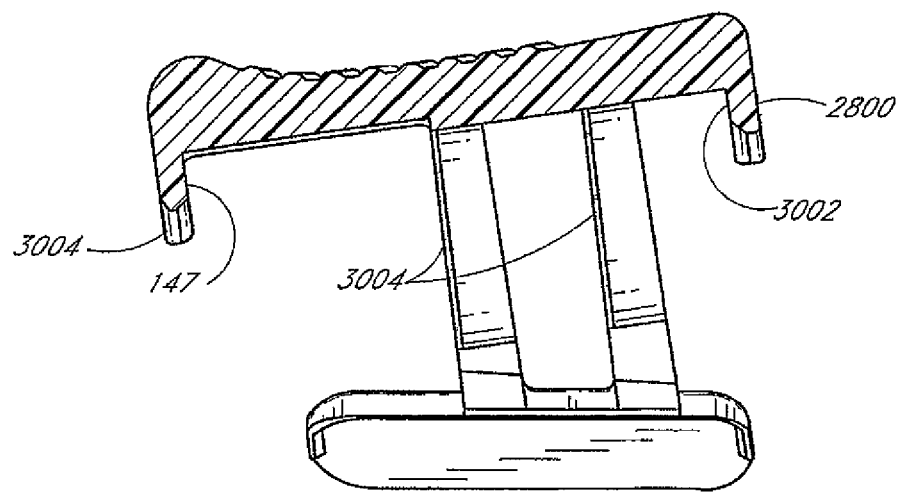
FIG. 30 is a cross section view taken along line 30-30 in FIG. 26 illustrating the abutment surfaces of the retainer.
Figure 33:
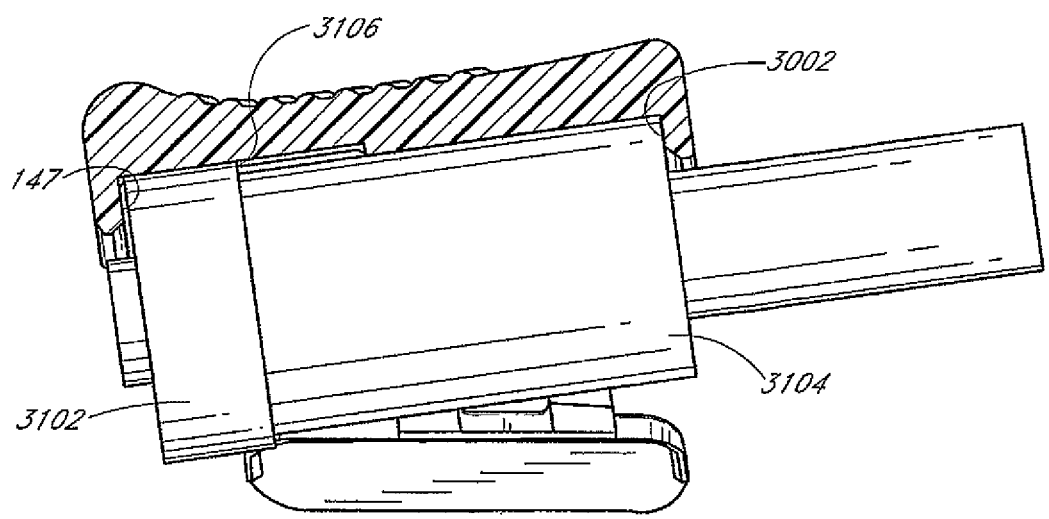
FIG. 33 is a cross section view taken along line 33-33 in FIG. 32 illustrating the abutment surfaces of the retainer in register with the contact surfaces of the medical article.
Figure 31:
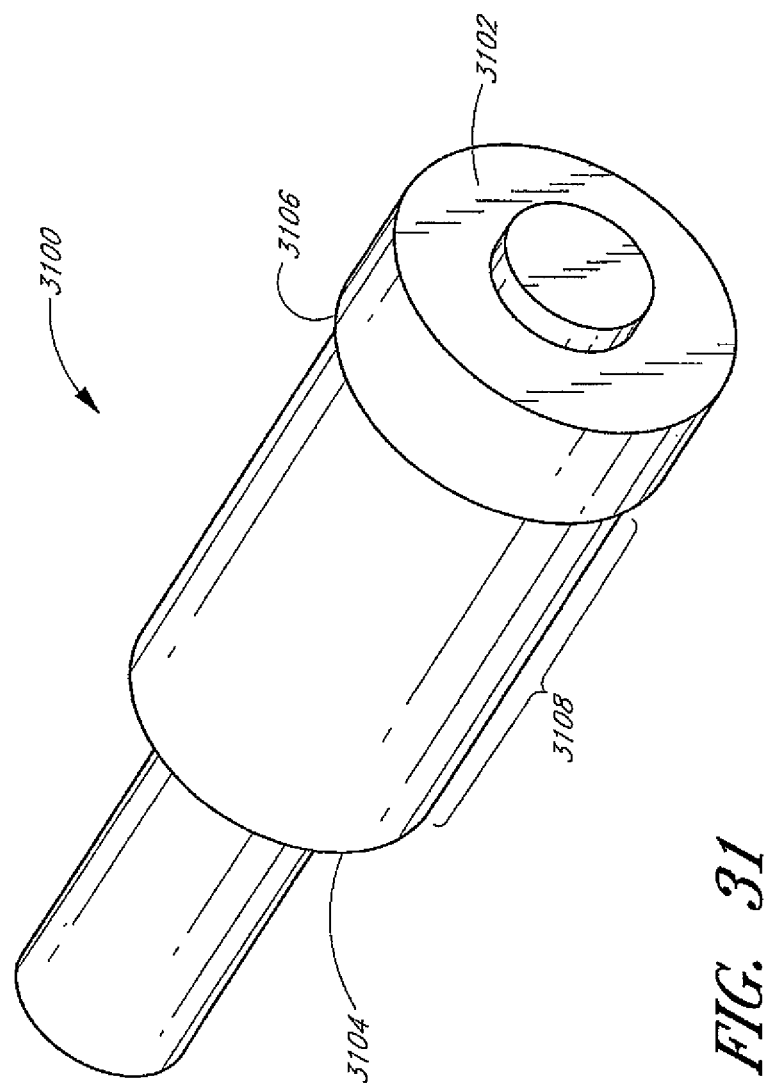
FIG. 31 is a simplified perspective view of a medical article that includes contact surfaces corresponding to the abutment surfaces illustrated in FIG. 30.
Figure 32:
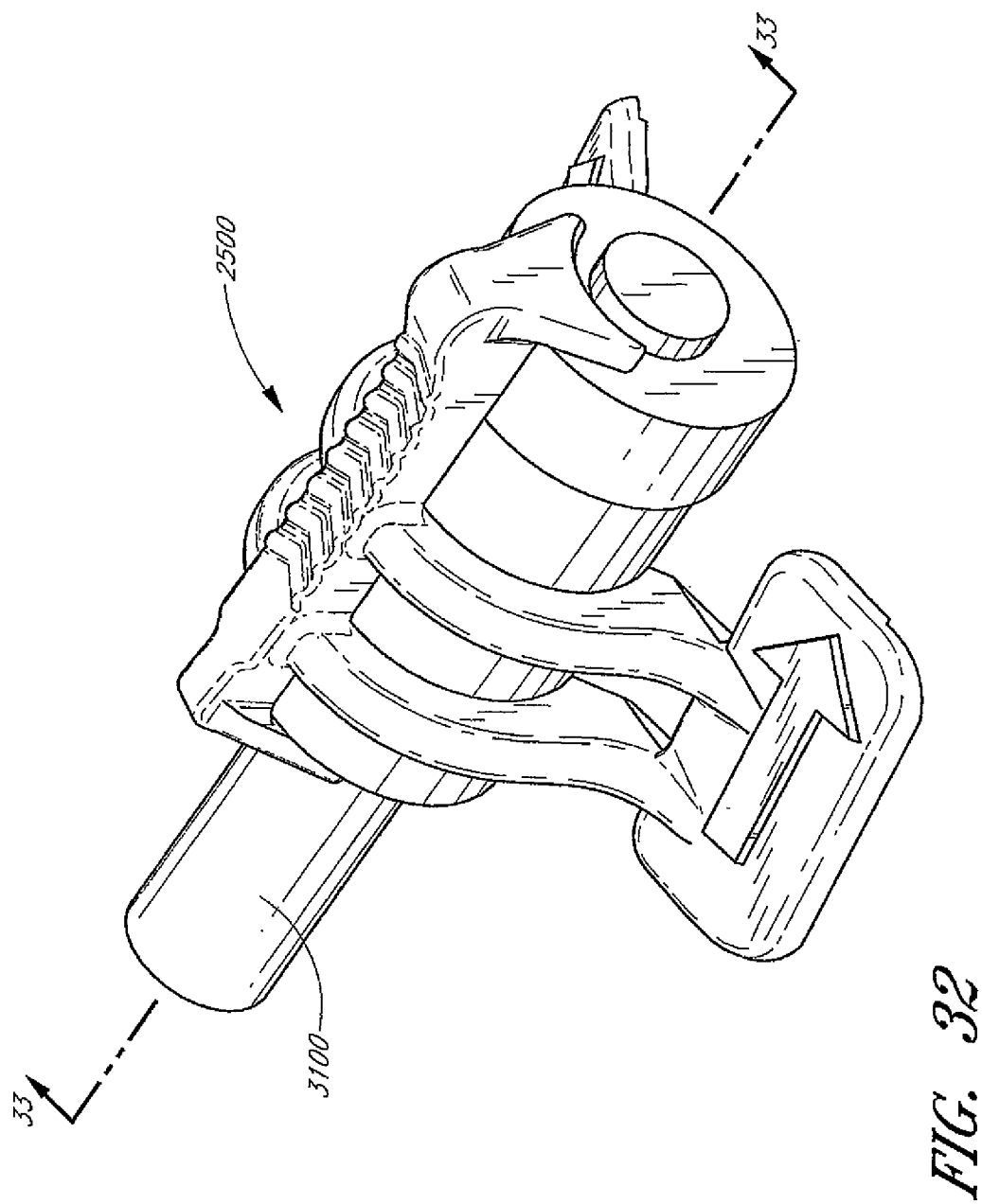
FIG. 32 is a perspective view of the medical article illustrated in FIG. 31 secured to the retainer of FIG. 25.
Figure 34:
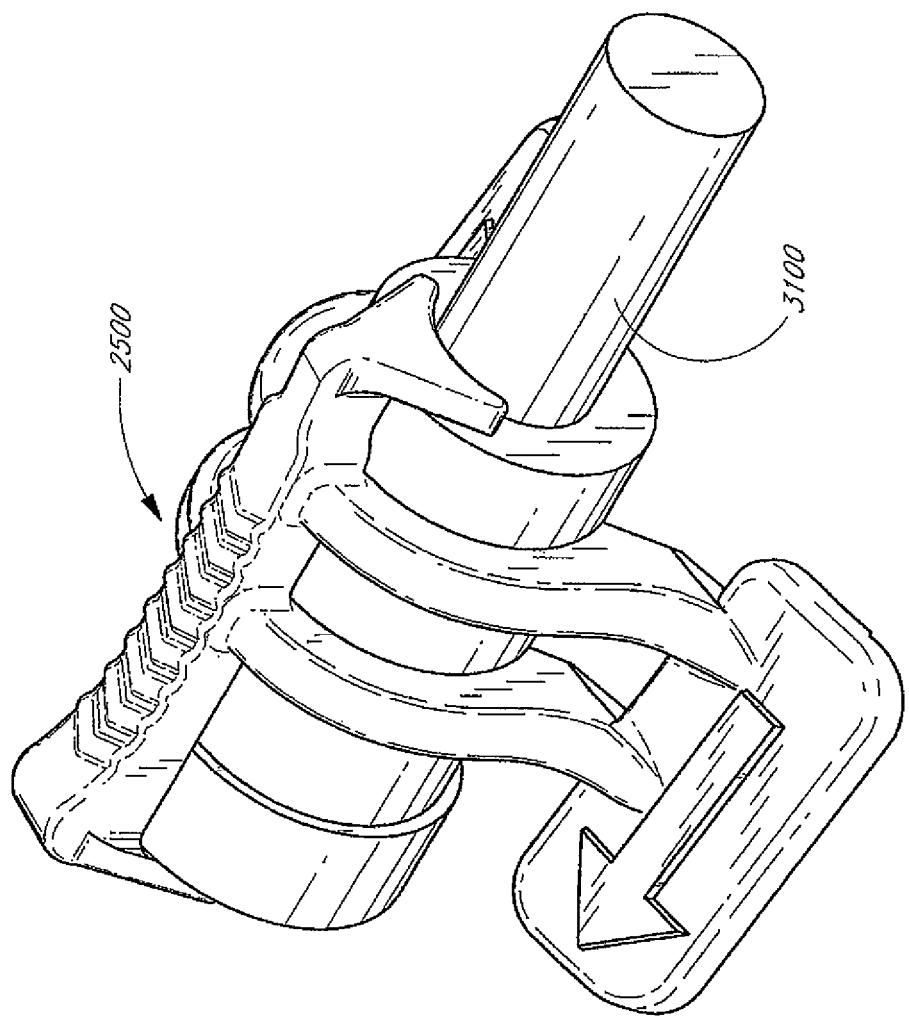
FIG. 34 is a second perspective view of the medical article illustrated in FIG. 31 secured to the retainer of FIG. 25.
Figure 35:
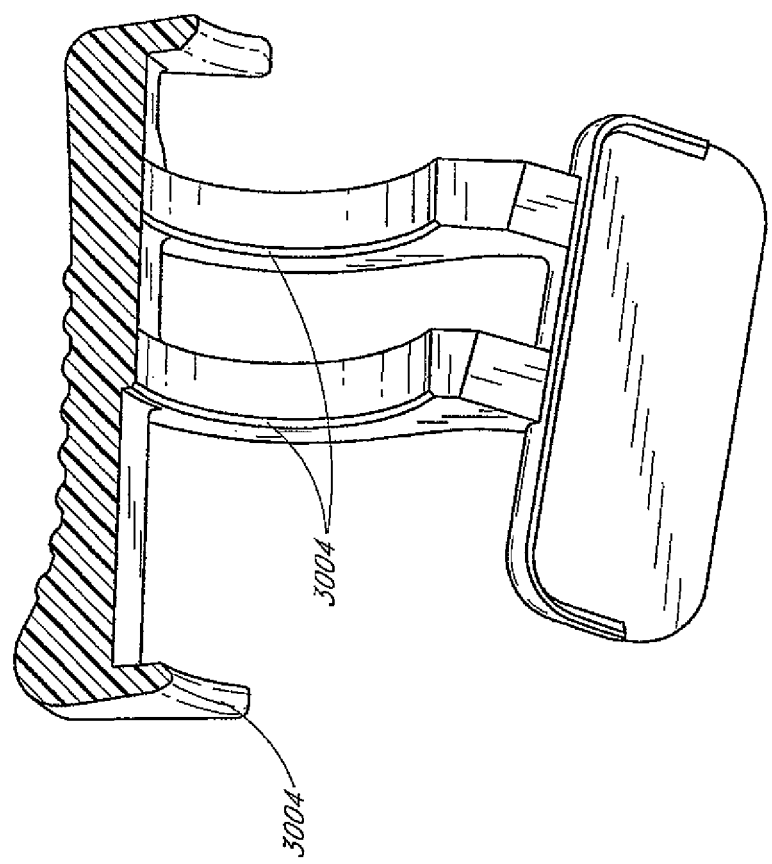
FIG. 35 is a perspective cross section view taken along line 30-30 in FIG. 26 illustrating chamfers or radiused regions on corners or edges of the retainer.

FIG. 6 illustrates another embodiment of a retainer 600 for use with a medical article as described with reference to FIG. 5. FIG. 6 is a perspective view of the retainer 600 and illustrates a movable spine 610 and corresponding ratchet 602 arrangement configured to receive and retain the spine 610 in multiple positions. The retainer 600 accommodates medical articles with different longitudinal lengths or in different longitudinal positions relative to the retainer. As shown in FIG. 6, the general structure of the retainer 600 is similar to that of the retainer 120 described with reference to FIGS. 2 through 5 except that the spine 145 and body member 130 described with reference to FIGS. 2 through 5 are separate members in FIG. 6 that slidably engage each other.

The spine 610 is slidably mounted on the retainer 600 and latches the connector fitting 300 to the retainer 600. The spine 610 includes a first interengagement structure which cooperates with a second interengagement structure of the ratchet 602 so as to permit motion of the spine 610 relative to the body member 130 in only one direction. In the embodiment illustrated in FIG. 6, the spine 610 moves in the distal direction.

Because the spine 610 is slidable, the retainer 600 accommodates variations in the longitudinal length of the radial extending member and/or variations in axial position of the connector fitting within the retainer. Preferably, the spine 610 has a somewhat flexible forked clip 147 that can be hooked over the proximal side of the radially extending member and accommodate variations in the diameter of the radial extending member. In certain embodiments, the shape or curvature of the clip 147 matches the outer surface of the body of the adapter hub 430 to stabilize the adapter hub 430.

The spine 610 has a middle neck portion with a generally flat rectangular shape. The proximal end of the spine 610 is free and extends downwardly below the outer surface of the radially extending member. The proximal end of the spine 610 is supported in cantilever fashion from the pawl 612 portion of the spine 610.

The ratchet element 602 is positioned on the radial outer top surface of the body member 130 and extends generally parallel to and spaced from the axis of the central channel 140. The ratchet element 602 connects to the body member 130 at a location between the mounting wings 210(a), 210(b). The body member 130 and the ratchet element 602 are preferably formed as one piece. The spine 610 is slidably mounted in this channel-like ratchet element 602.

The spine 610 and the ratchet element 602 include at least one row of interengaging ratchet teeth 604 or interengaging pawls 612 on their side edges for maintaining the spine 610 in a manually selected position. The ratchet teeth 604 are formed on the inner sides or lateral, flat surfaces of the ratchet element 602 and are aligned in a longitudinal direction with each tooth extending radially towards the longitudinal axis. In a preferred form of the invention, the ratchet teeth 604 are formed in only a portion of the side walls of the channel-like ratchet element 602. The interengaging pawl 612 is resiliently formed into a portion of the sides of the spine 610 and is aligned so as to be parallel to the side walls of the channel-like ratchet element 602. The interengaging pawl 612 cooperates with the teeth of the ratchet element 602 to manually fix the position of the forked clip 147 or proximal end of the spine 610.

The spine 610 and the ratchet element 602 further include an interengaging tongue 508 portion and corresponding groove(s) 606, respectively. In a preferred form, the grooves 606 are formed in portions of the side walls of the channel-like ratchet element 602 that are located below the teeth 604 and above a bottom surface of the channel-like ratchet element 602. The tongue 608 is formed along a lower portion of the spine 610 and extends parallel to the pawls 612. At least a portion of the tongue 608 extends in a lateral direction beyond at least a portion of the jagged outer periphery of the pawl 612. The tongue 608 and grooves 606 cooperate to guide the pawls 612 between the facing rows of teeth 604 and further limit transverse movement of the spine 610 relative to the body member 130 when the tongue 608 is seated within the grooves 606. Thus, the combination of the engagement between the teeth 604 and the pawl 612 along with the engagement between the tongue 608 and the grooves 606 inhibits transverse, lateral, and proximal longitudinal movements of the spine 610 relative to the body member 130.

Alternatively, the location of the pawls 612, the teeth 604, the tongue 608 and the grooves 606 are reversed. In such an arrangement, the pawls 612 and teeth 604 are located below the tongue 608 and grooves 606.

Alternatively, both rows of teeth 604 are slightly rotated towards each other and about axes which are parallel to the longitudinal axis to form a channel-like ratchet element 602 with side walls that converge in a radial direction away from the longitudinal axis. The sides of the pawl 612 are angled towards each other so as to align with the teeth 604 when the spine 610 is inserted into the ratchet element 602. By angling the walls of the teeth 604 and pawls 612, the engagement between the teeth 604 and the pawl 612 inhibits transverse, lateral, and proximal longitudinal movements of the spine 610 relative to the body member 130 without a tongue 608 and groove 606 arrangement.

Because conventional medical articles have dimensional variations, it is desirable that the spine 610 be adjustable to accommodate the various sizes and yet securely hold the medical article relative to the retainer 600. The spine 610 is easily movable distally along the ratchet element 602, and the ratchet teeth 604 cooperate with the clip pawl 612 to resist proximal movement and hold the spine 610 in the manually selected position.

The spine 610 is preferably made from a stiff but somewhat flexible plastic. Thus, although the pawl 612 and ratchet teeth 604 are relatively stiff so as to fix the pawl 612 when engaged with the ratchet teeth 604, the clip 147 can pivot somewhat about the body member 130. The ease at which the clip 147 pivots is enhanced by reducing the cross-sectional area of the neck portion of the spine 610 relative to the cross-sectional area of the distal portion of the pawl 612. Pulling the spine 610 in a radial direction away from the longitudinal axis will correspondingly move the clip 147 away from the retained medical article. Thus, bending the forward or proximal end of the spine 610 in a radial and outwardly direction away from the longitudinal axis 260, with the spine 610 mounted within the ratchet element 602 of the retainer 600, allows the forked end of the clip to engage and disengage from the radial extending member of the retained medical article. Withdrawing the bending force allows the forked end of the spine 610 to return inwardly to its normal latching position. The clip 147 can further function as a stop which extends towards the longitudinal axis and limits the movement of the spine 610 in the distal direction.

As with the embodiment described with reference to FIGS. 2-5, the connector fitting 300 (see FIG. 5) is inserted through the opening 150 and into the central channel 140 of the body member 130. The contact surfaces of the connector fitting preferably form one or more radially extending members (e.g., a spin nut 330). The radially extending member contacts the clip 147 to thereby inhibit proximal transverse movement of the medical article relative to the retainer 120.

The mounting wings 210(a), 210(b) are mounted upon the anchor pads (not shown) and the anchor pads are secured to the skin of the patient, generally by an adhesive disposed upon the bottom surface of each pad. In this way, the retainer 600 secures the medical article to the patient.

The embodiments of the retainer illustrated in FIGS. 1-5 and FIG. 6 arrest at least longitudinal motion of an exemplary medical article having two contact surfaces in the form of a single radially extending member or spin nut. Preferably, when the connector fitting is installed in the channel 140 of the retainer, a radially extending member or spin nut extends between the distal side of the clip 147 of the spine 145 and the proximal end 127 of the retainer body 130 (See FIG. 5). The distal side of the clip 147 and the proximal end 127 of the retainer body or ribs 280 each form an abutment surface. Contact between these two abutment surfaces on the retainer and the corresponding contact surfaces on the medical article arrests motion in both longitudinal directions. The embodiments illustrated in FIGS. 1-5 and 6 preferably locate a spin nut between the proximal end 127 of the retainer body 130 and the distal side of the clip 147.

FIGS. 7 through 15, 16 through 24, and 25 through 35 each illustrate an exemplary embodiment of a retainer having a central channel 140 configured to receive at least a portion of the radially extending member or spin nut of the medical article between the proximal 127 and distal 125 ends of the retainer body 130. Unlike the embodiments illustrated in FIGS. 1-5 and 6, at least a portion of the radially extending member or spin nut of the medical article is located between the distal 125 and proximal 127 ends of the retainer body 130.

The embodiments of the retainer illustrated in FIGS. 7 through 15, 16 through 24, and 25 through 35 include one or more abutment surfaces that are located between the proximal 127 and distal 125 ends of the retainer body 130 (FIGS. 7-15, 16-24) or outside of the region between the distal 125 and proximal 127 ends (FIGS. 25-35). Of course a combination of abutment surfaces located inside and outside of the body 130 is within the scope of the invention. While each embodiment of the retainer is illustrated as having a certain number of abutment surfaces they may include fewer or more abutment surfaces. Preferably, the embodiments of the retainer described with reference to FIGS. 7 through 15, 16 through 24, and 25 through 35 include at least two abutment surfaces to arrest longitudinal motion in both directions. For example, the embodiment illustrated with reference to FIGS. 7 through 15 has two abutment surfaces located between the proximal and distal ends of the retainer. The embodiment illustrated with reference to FIGS. 16 through 24 has a single abutment surface located between the proximal and distal ends of the retainer. The embodiment illustrated with reference to FIGS. 25 through 35 has two abutment surfaces located outside of the region between the proximal and distal ends of the retainer.

A retainer having a single abutment surface may incorporate an additional retention feature which in combination with the single abutment surface arrests longitudinal motion in both directions. These additional retention features include, for example, an adhesive material or high friction material located on a surface of the retainer contacting the retained medical device. For example, an adhesive may be located on the central channel 140 or on the single abutment surface.

The embodiment of the retainer 700 illustrated in FIGS. 7 through 15 comprises at least three abutment surfaces 147, 1200, 1202. As shown most clearly in FIGS. 12 and 13, a first exemplary abutment surface 147 is located on the distal side of the clip and corresponds to a contact surface 1304 on the medical article 1306 to be retained. A second exemplary abutment surface 1200 is located between the distal 125 and proximal 127 ends of the retainer 700 and corresponds to a contact surface 1300 on the medical article. A third abutment surface 1202 is located between the distal 125 and proximal 127 ends of the retainer 700. The third abutment surface 1202 corresponds to a contact surface 1302 on the medical article.

As shown in FIGS. 7 through 15, the general structure of the retainer 700 is similar to that of the retainer 120 described with reference to FIGS. 1 through 5 except that the body member 130 of the retainer 700 includes abutment surfaces 1200, 1202 which are located between the proximal and distal ends of the retainer body 130. These abutment surfaces 1200, 1202 correspond to contact surfaces 1300, 1302 on the exemplary medical article illustrated in FIG. 13. Contacts between the abutment surface on the clip 147 and at least one of the abutment surfaces 1300, 1302 on the retainer and the corresponding contact surfaces on the medical article arrest motion in both longitudinal directions. The abutment surfaces of the retainer 700 are preferably used with a KIPP micro design catheter device. However, the retainer 700 may be used with other retainer designs.

The embodiment of the retainer 1600 illustrated in FIGS. 16 through 24 comprises at least two abutment surfaces 147, 2100. As shown most clearly in FIGS. 21 and 22, a first exemplary abutment surface of the clip 147 is located on the distal side of the lip and corresponds to a contact surface 2204 on the medical article 2200 to be retained. A second exemplary abutment surface 2100 is located between the distal 125 and proximal 127 ends of the retainer 1600 and corresponds to a contact surface 2206 on the medical article. A third abutment surface 2102 is located between the distal 125 and proximal 127 ends of the retainer 1600. The medical article does not include a contact surface corresponding to the third abutment surface 2102.

As shown in FIGS. 16 through 24, the general structure of the retainer 1600 is similar to that of the retainer 120 described with reference to FIGS. 1 through 5 except that the body member 130 of the retainer 1600 includes an abutment surface 2100 which is located between the proximal and distal ends of the retainer body 130. The abutment surface 2100 corresponds to contact surface 2206 on the medical article illustrated in FIG. 22. Contact between the first abutment surface on the clip 147 and the second abutment surface 2100 with the corresponding contact surfaces on the medical article arrests motion in both longitudinal directions. The abutment surfaces of the retainer 1600 are preferably used with a KIPP macro design catheter device. However, the retainer 1600 may be used with other retainer designs.

The embodiment of the retainer 2500 illustrated in FIGS. 25 through 34 comprises at least two abutment surfaces 147, 3002. As shown most clearly in FIGS. 30 and 31, a first exemplary abutment surface is located on the distal side of the clip 147 and corresponds to a contact surface 3102 on the medical article 3100 to be retained. A second exemplary abutment surface 3002 is located on the proximal side of the clip 2800 and corresponds to a contact surface 3104 on the medical article. As shown in FIGS. 25 through 34, the general structure of the retainer 2500 is similar to that of the retainer 120 described with reference to FIGS. 1 through 5 except that the body member 130 of the retainer 2500 includes a second spine 2800 extending in a proximal direction. In this way, the retainer 2500 includes spines 145, 2800 extending in both the proximal and distal directions from the body member 130. Contact between the first and second abutment surfaces 147, 3002 on the retainer and the corresponding contact surfaces on the medical article arrests motion in both longitudinal directions. The abutment surfaces of the retainer 2500 are preferably used with an AbbottMacro design catheter device. However, the retainer 2800 may be used with other retainer designs.

The retainers may include chamfers or radiused regions on corners or edges of the retainers. As most clearly shown in FIGS. 30 and 35, the retainer 2500 includes chamfers 3004 on one or more of the proximal edges of the ribs 280 and/or spine 145 of the retainer body 130. Preferably, a radius on a bottom surface of the spine 145 is selected to match a radius of curvature of the medical article 3100. In certain embodiments, the bottom surface of the spine 145 matches a radius of the medical article in region 3108 (see FIG. 31). The chamfers 3004 in combination with the matched radius may ease any required longitudinal movement of the retainer 2500 along an outer surface of the medical article 3100 during installation. For example, if a medical provider installs the retainer 2500 over the medical article 3100 such that the region located between the abutment surfaces 147, 3002 is not aligned with the region located between the contact surfaces 3102, 3104, the retainer body 130 may be slid in a longitudinal direction relative to the medical article until the contact surfaces and the abutment surfaces are aligned. The chamfers 3004 on the proximal edges of the ribs 280 and spine 145 may prevent those surfaces from binding on any circumferential ridges or steps in the body of the medical article.

Without the chamfers 3004, ridge 3106 (see FIG. 33) on the exemplary medical article 3100 may inhibit a medical provider from sliding the retainer 2500 in a proximal and longitudinal direction relative to the medical article 3100. With the chamfers 3004, the radius on the bottom surface of the spine 145 slides over the ridge 3106 and continues sliding along the outer surface of the medical article until the abutment surface 3002 contacts the contact surface 3104. Preferably, prior to the abutment surface 3002 contacting the contact surface 3104, the spine 145 will have snapped over the contact surface 3102. In this way, motion of the retainer 2500 in the opposite or distal direction is inhibited by contact between the contact surface 3102 and the abutment surface of the clip 147.

The various embodiments of securement devices and techniques described above thus provide a number of ways to provide safe and releasable securement for medical articles to the skin of a patient. In addition, the techniques described may be broadly applied for use with a variety of medical lines and medical procedures.

Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and systems have been disclosed in the context of certain embodiments and examples, it will be understood by those skilled in the art that these techniques and systems may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above.

What is claimed is:

1. A retainer for securing a medical article having a spin nut to a patient, the retainer comprising:
   two anchor pads, each including a lower adhesive surface for attaching to an epidermal layer of a patient and an upper surface;
   two supports attached to the upper surfaces of the two anchor pads;
   a curved rib connecting the two supports and having a downward facing interior, the interior having a truncated cross-sectional shape and being configured to receive at least a portion of the medical article in a snap fit manner so as to inhibit at least downward transverse movement of the medical article when the medical article is secured within the retainer, the rib having a first abutment disposed on a proximal side of the rib;
   a longitudinal access opening disposed on an underside of the curved rib to allow at least ingress of the portion of the medical article between the two supports and into the rib interior; and
   a cantilevered spine extending in a proximal direction from the rib and having a clip end, the clip end having a second abutment spaced a distance from the first abutment, the distance between the first abutment and the second abutment generally corresponding to a width of a spin nut, the spine being spaced in a transverse direction from the upper surfaces of the anchor pads, at least a portion of the spine between the rib and the second abutment of the clip end configured to contact the medical article so as to prevent upward transverse movement of the medical article.

2. A retainer as in claim 1 further comprising a second curved rib disposed on a distal side of the first rib and connecting the two supports, the second rib having an interior shaped to retain at least a portion of the medical article.

3. A medical line securement system comprising:
   a medical article;
   two anchor pads, each including a lower adhesive surface configured to attach to an epidermal layer of a patient and an upper surface; and
   a retainer comprising,
      a body member having a channel formed therethrough about a channel axis, the channel being configured to retain at least a portion of the medical article and having a longitudinal access opening disposed on an underside of the body member to allow at least ingress of the portion of the medical article into the channel,
      a cantilevered spine extending parallel to the channel axis in a proximal direction from the body member and having an abutment on a distal end of the spine, the spine being spaced in a transverse direction from the upper surfaces of the two anchor pads, the abutment extending generally normal to the channel axis and configured to inhibit longitudinal movement of the medical article, at least a portion of the spine between the body member and the abutment contacting the medical article so as to prevent upward transverse movement of the medical article, and
      two supports disposed on the underside of the retainer and to both sides of the access opening opposite the channel axis, the supports being attached to the upper surfaces of the two anchor pads.

4. A medical line securement system as in claim 3, wherein the channel further comprises an inner surface, at least a portion of said inner surface coated with an adhesive and configured to contact the portion of the medical article.

5. A medical line securement system as in claim 4, wherein the portion of said inner surface coated with the adhesive is located opposite the longitudinal access opening.

6. A medical line securement system as in claim 3, wherein the medical article comprises at least one contact surface which is configured to abut against the abutment to arrest movement of the medical article in at least one direction.

7. A medical line securement system as in claim 3, wherein the medical article comprises two contact surfaces, and wherein a distance between the first abutment and a second abutment is sized to receive the two contact surfaces therebetween.

8. A medical line securement system as in claim 3, wherein the body member comprises at least two ribs connecting the two supports.

9. A medical line securement system comprising:
a medical article having a distal facing contact surface and a proximal facing contact surface;
two anchor pads, each including a lower adhesive surface for attaching to an epidermal layer of a patient and an upper surface; and
a retainer comprising,
two supports attached to the upper surfaces of the two anchor pads;
a curved rib connecting the two supports and having a downward facing interior, the interior being shaped to retain at least a portion of the medical article and inhibit at least downward transverse movement of the medical article when the medical article is secured within the retainer, the rib having a first abutment disposed on a proximal side of the rib and contacting the distal facing contact surface of the medical article so as to inhibit distal longitudinal movement of the medical article if the medical article is slid in a distal longitudinal direction through the interior of the rib;
a longitudinal access opening disposed on an underside of the curved rib to allow at least ingress of the portion of the medical article between the two supports and into the rib interior; and
a cantilevered spine extending in a proximal direction from the rib and having a clip spaced a distance from the rib, the spine being spaced in a transverse direction from the upper surfaces of the two anchor pads, the clip having a second abutment disposed on a distal side of the clip and contacting the proximal facing contact surface of the medical article so as to inhibit proximal movement of the medical article if the medical article is slid in a proximal longitudinal direction through the interior of the rib, at least a portion of the spine between the rib and the second abutment of the clip contacting the medical article so as to prevent upward transverse movement of the medical article.

10. A medical line securement system as in claim 9, wherein at least a portion of the rib interior is coated with an adhesive for contacting and securing the secured portion of the medical article.

11. A medical line securement system as in claim 10, wherein the adhesive is located on an opposite side of the longitudinal access opening.

12. A medical line securement system as in claim 9 further comprising a second curved rib connecting the two supports, the second rib having an interior shaped to retain at least a portion of the medical article.

13. A medical line securement system as in claim 12, wherein the second curved rib connects to the spine and is disposed on a distal side of the first rib.

14. A medical line securement system as in claim 9, wherein the distance between the first abutment and the second abutment is adjustable.

15. A medical line securement system as in claim 9, wherein a distance between the first and second abutments in the longitudinal direction is fixed.

16. A medical line securement system as in claim 15, wherein the spine is movable in a direction away from a longitudinal axis through the interior of the rib.

17. A medical line securement system as in claim 9, wherein the second abutment does not move in at least the longitudinal direction relative to the first abutment.

18. A medical line securement system as in claim 17, wherein the spine is movable in a direction away from a longitudinal axis through the interior of the rib.

* * * * *